US012036275B2

(12) United States Patent
Seele et al.

(10) Patent No.: US 12,036,275 B2
(45) Date of Patent: Jul. 16, 2024

(54) **VACCINE COMPOSITION AGAINST *STREPTOCOCCUS SUIS* INFECTION**

(71) Applicant: Ceva Santé Animale S.A., Libourne (FR)

(72) Inventors: Jana Seele, Hannover (DE); Christoph Baums, Leipzig (DE); Peter Valentin-Weigand, Ilsede (DE)

(73) Assignee: Ceva Santé Animale S.A., Libourne (FR)

( * ) Notice: Subject to any disclaimer, the term of this patent is extended or adjusted under 35 U.S.C. 154(b) by 173 days.

(21) Appl. No.: 16/985,589

(22) Filed: Aug. 5, 2020

(65) Prior Publication Data

US 2021/0015910 A1 Jan. 21, 2021

Related U.S. Application Data

(63) Continuation of application No. 15/314,597, filed as application No. PCT/EP2015/061961 on May 29, 2015, now abandoned.

(30) Foreign Application Priority Data

May 30, 2014 (EP) .................................... 14170637

(51) Int. Cl.
*A61K 39/09* (2006.01)
*A61K 39/00* (2006.01)
*C07K 16/12* (2006.01)

(52) U.S. Cl.
CPC ........ *A61K 39/092* (2013.01); *C07K 16/1275* (2013.01); *A61K 2039/53* (2013.01); *A61K 2039/54* (2013.01); *A61K 2039/543* (2013.01); *A61K 2039/545* (2013.01); *A61K 2039/552* (2013.01); *A61K 2039/575* (2013.01)

(58) Field of Classification Search
CPC .............. A61K 39/092; A61K 2039/53; A61K 2039/54; A61K 2039/543; A61K 2039/545; A61K 2039/552; A61K 2039/575; C07K 16/1275
See application file for complete search history.

(56) References Cited

U.S. PATENT DOCUMENTS

2017/0209561 A1 7/2017 Seele et al.

FOREIGN PATENT DOCUMENTS

WO WO 2004/020618 3/2004

OTHER PUBLICATIONS

Baums et al. (2009) Surface-associated and secreted factors of *Streptococcus suis* in epidemiology pathogenesis and vaccine development. Animal Health Research Reviews. 10(1):65-83.

Bork (Genome Research, 2000, 10:398-400) (Year: 2000).

Boslego et al (Vaccines and Immunotherapy, 1991, Chapter 17) (Year: 1991).

Bowie et al (Science, 1990, 257:1306-1310) (Year: 1990).

Burgess et al (J. of Cell Bio. 111:2129-2138, 1990) (Year: 1990).

Campbel, A. M. (Monoclonal Antibody Technology, Elsevier, NY. 1984; chapter 1, pp. 1-32) (Year: 1984).

Ellis (Vaccines, W.B. Saunders Company, Chapter 29, 1988, pp. 568-574) (Year: 1988).

Holden et al. (2009) Rapid evolution of virulence and drug resistance in the emerging zoonotic pathogen *Streptococcus suis*. PLOS One. 4(7)E6072:1-17.

Hulting et al. (2009) Two novel IgG endopeptidases of *Streptococcus equi*. FEMS Microbiology Letters. 298(1):44-50.

International Preliminary Report on Patentability corresponding to International Patent Application No. PCT/EP2015/061961 dated Dec. 6, 2016.

International Search Report corresponding to International Patent Application No. PCT/EP2015/061961 dated Jul. 27, 2015.

Lazar et al. (Molecular and Cellular Biology, 1988, 8:1247-1252) (Year: 1988).

Office Action corresponding to U.S. Appl. No. 15/314,597 dated Feb. 6, 2020.

Office Action corresponding to U.S. Appl. No. 15/314,597 dated May 2, 2019.

Office Action corresponding to U.S. Appl. No. 15/314,597 dated Nov. 24, 2017.

Office Action corresponding to U.S. Appl. No. 15/314,597 dated Sep. 13, 2018.

Seele et al. (2013a) Identification of a novel host-specific IgM protease in *Streptococcus suis*. Journal of Bacteriology. 195(5):930-940.

Seele et al. (2013b) Identification of a novel host-specific IgM protease in *Streptococcus suis*. Journal of Bacteriology. 195(5):930-940. Supplemental material.

Seele et al. (2015a) The immunoglobulin M-degrading enzyme of *Streptococcus suis*, IdeSsuis, is involved in complement evasion. Veterinary Research 46(1):45.

Seele et al. (2015b) The immunoglobulin M-degrading enzyme of *Streptococcus suis*, IdeSsuis, is a highly protective antigen against serotype 2. Vaccine. 33(19):2207-2212.

Skolnick et al. (Trends in Biotechnology 18: 34-39, 2000) (Year: 2000).

(Continued)

*Primary Examiner* — Robert A Zeman
(74) *Attorney, Agent, or Firm* — Oblon, McClelland, Maier & Neustadt, L.L.P.

(57) ABSTRACT

Described is a vaccine composition comprising an effective amount of at least one polypeptide selected from the group of IdeSsuis, rIdeSsuis, an analogue or a fragment thereof, or a polynucleotide encoding the same. This vaccine composition is used in the prophylactic, metaphylactic or therapeutic treatment of a *Streptococcus suis* infections in pigs or humans.

10 Claims, 4 Drawing Sheets

Specification includes a Sequence Listing.

(56) References Cited

OTHER PUBLICATIONS

UniProt Accession No. B9WTH0; [Online] (Apr. 14, 2009) SubName: Full=Mac 1 domain protein {EC0:0000313:EMBL:EEF65121.1} Flags:Precursor.
UniProt Accession No. C5W022 [Online] (Sep. 2009) RecName: Full=IgM protease; EC=3.4.22.-;AltName: Full=Immunoglobulin M-degrading enzyme of *S. suis*; Short=IdeSsuis; Flags: Precursor;. retrieved from EBI accession No. UNIPROT:C5W022. Database accession No. C5W022 sequence.
Wisselink et al. (2001) Protection of Pigs Against Challenge with Virulent *Streptococcus suis* Serotype 2 Strains by a Muramidase-Released Protein and Extracellular Factor Vaccine. Veterinary Record. British Veterinary Association. 148(15):473-477.
Written Opinion of the International Searching Authority corresponding to International Patent Application No. PCT/EP2015/061961 dated Dec. 3, 2015.
Zhang et al. (2011) Comparative genomic analysis of *Streptococcus suis* reveals significant genomic diversity among different serotypes. BMC Genomics. Biomed Central Ltd. 12(1):523.
Canadian Office Action issued on Mar. 18, 2022 in Patent Application No. 2,947,798, 4 pages.
Search Report issued May 31, 2022, in corresponding Maylaysian Patent Application No. PI2020000533.
Christoph Georg Baums et al, "Surface-Associated and Secreted Factors of *Streptococcus suis* in Epidemiology Pathogenesis and Vaccine Development", *Animal Health Research Reviews*, vol. 10, No. 1, Jun. 1, 2009, pp. 65-83.
Greta Hulting et al, "Two Novel IgG Endopeptidases of *Streptococcus equi", FEMS Microbiology Letters,* Vo. 298, No. 1, Sep. 1, 2009, pp. 44-50.
Anding Zhang, et al, "Comparative Genomic Analysis of *Streptococcus suis* Reveals Significant Genomic Diversity Among Different Serotypes", *BMC Genomics Biomed Central Ltd. London, UK,* vol. 12, No. 1., Oct. 25, 2011 pp. 523.
Matthew T.G. Holden, et al., "Rapid Evolution of Virulence and Drug Resistance in the Emerging Zoonotic Pathogen *Streptococcus suis", PLOS One,* vol. 4, No. 7, Jul. 2009, pp. 1-17.

| number of pigs | 1. immunization | 2. immunization | challenge |
|---|---|---|---|
| 9 | rideSsuis (0.4mg/piglet) | rideSsuis (0.25mg/piglet) + bacterin (S. suis serotype 2 strain \|9841) | S. suis serotype 2 strain 10 |
| 9 | rideSsuis (0.4mg/piglet) | rideSsuis (0.25mg/piglet) | S. suis serotype 2 strain 10 |
| 8 | placebo | bacterin (S. suis serotype 2 strain \|9841) | S. suis serotype 2 strain 10 |
| 9 | placebo | placebo | S. suis serotype 2 strain 10 |

- vs. prime bacterin : $p=0.8237$

- vs. prime and booster rideSsuis: $p=0.0031$

- vs. prime and booster rideSsuis + prime bacterin: $p=0.0013$ prime bacterin vs. prime and booster rideSsuis: $p=0.0031$ prime bacterin vs. prime and booster rideSsuis + prime bacterin: $p=0.0013$

SEQUENCE LISTING

```
<160> NUMBER OF SEQ ID NOS: 14

<210> SEQ ID NO 1
<211> LENGTH: 1141
<212> TYPE: PRT
<213> ORGANISM: Streptococcus suis

<400> SEQUENCE: 1

Met Asn Ile Gln Glu Arg Phe Ser Leu Arg Lys Ser Ala Val Gly Leu
1               5                   10                  15

Val Ser Val Ser Leu Leu Cys Ala Ile Tyr Thr Ser Thr Val Ala Ala
            20                  25                  30

Asp Thr Val Val Thr Gly Val Asn Glu Ile Ile Glu Glu Ser Gln Val
        35                  40                  45

Lys Asp Glu Val Ser Ile Glu Ser Glu Lys Asn Glu Ser Leu Asp Gly
    50                  55                  60

Ser Asn Ile Glu Ile Val Glu Glu Ile Ala Asp Asn Ile Pro Ser Pro
65                  70                  75                  80

Val Ile Ala Glu Gly Glu Val Ala Val Glu Met Lys Val Asp Arg Gly
                85                  90                  95

Thr Glu Asn Val Val Ser Arg Asn Asp Thr Glu Val Thr Thr Ser Glu
            100                 105                 110

Gln Asn Gln Ile Glu Val Thr Glu Thr Lys Glu Ile Leu Asn Gln Thr
        115                 120                 125

Ser Tyr Gln Thr Glu Ser Gly Glu Gln Arg Gln Ile Ile Trp Ala His
    130                 135                 140
```

-continued

```
Gly Ile Thr Pro Pro Ala Met Glu Gln Ser Gly Gly Phe Val Lys Glu
145                 150                 155                 160

Lys Tyr Gly Asp Tyr Leu Asn Tyr Thr Ala Pro Phe Glu Ala Gly Lys
                165                 170                 175

Gly Tyr Tyr Asp Thr Asn Lys Ser Leu Asn Ala Ser Phe Ile Asp Leu
            180                 185                 190

Asn Leu Cys Phe Ala Ala Val Ser Ser Asn Met Val His Trp Trp Leu
        195                 200                 205

Glu Gln Asn Ser Ser Tyr Val Glu Arg Tyr Leu Lys Glu Lys Lys Gly
    210                 215                 220

Thr Val Asn Val Glu Glu Asn Tyr Ala Ile Thr Asp Leu Arg Arg Tyr
225                 230                 235                 240

Ile Asn Ser Phe Gln Asn Gln Gln Asn Ser Arg Val Phe Asp Met Phe
                245                 250                 255

Lys Thr Tyr Tyr Gly Tyr Arg Thr Asn Gly Phe Val Ser Asp Ala Leu
            260                 265                 270

Val Asp Leu Phe Ile Asn Gly Tyr Lys Pro Lys Ala Gln Gly Gly Val
        275                 280                 285

Asn Leu Glu Asp Ser Gln Leu Val Pro Asp Ser Arg Gly Gly Phe Phe
    290                 295                 300

Tyr Asp Val Phe Lys Glu Lys Lys Leu Thr Asn Arg Ile Phe Ser Gly
305                 310                 315                 320

Ser Tyr Glu Arg Phe Gly Glu Asp Val Arg Thr Val Leu Glu Ser Lys
                325                 330                 335

Gly Leu Leu Gly Leu Thr Tyr Arg Thr Leu Gly Tyr Ala Thr His Ile
            340                 345                 350

Val Thr Val Trp Gly Ala Glu Tyr Asp Asn Gln Gly Lys Ile Lys Ala
        355                 360                 365

Val Tyr Ile Thr Asp Ser Asp Asp Gln Gln Glu Gln Ile Gly Leu Lys
    370                 375                 380

Arg Met Gly Ile Thr Arg Asp Ala Ser Gly Asn Pro Arg Leu Asn Asn
385                 390                 395                 400

His Met Lys Asn Asn Ser Ala Gly Ala Leu Leu Asp Tyr Val His Thr
                405                 410                 415

Ile Arg Leu Gly Gln Asp Leu Trp Glu Glu Tyr Phe Asn Pro Leu Ala
            420                 425                 430

Lys Ala Lys Glu Thr Ala Ser Gln Thr Leu Ala Asp Thr Lys Lys Ala
        435                 440                 445

Leu Asp Leu Ser Ile Gln Gly Gln Ser Glu Leu Pro Glu Ser Met Arg
    450                 455                 460

Leu Ile Tyr Leu Glu Lys Leu Asn Asn Leu Tyr Asn Gln Gly Ile Leu
465                 470                 475                 480

Ser Ile Gln Lys Ala Glu Ser Ser Glu Met Leu Ser Gly Ala Leu Glu
                485                 490                 495

Asn Gly Leu Asn Ser Leu Lys Ser Leu Asp Phe Pro Ile Ser Glu Val
            500                 505                 510

Gly Asn Ala Leu Ala Pro Asp Leu Pro Val Gly Asp Arg Ser Thr Val
        515                 520                 525

Ser Asp Val Asp Ser Leu Ser Ser Gln Glu Thr Ser Ser Thr Asn Leu
    530                 535                 540

Glu Ala Asp Thr Glu Asn Ala Gly Ile Ile Ala Asp Gly Thr Asn Gln
545                 550                 555                 560
```

-continued

```
Leu His Phe Pro Val Glu Ala Gln Thr Thr Ser Ser Val Glu Ala Glu
                565                 570                 575

Gly Asp Asn Val Phe Glu Gln Glu Ala Asp Thr Leu Pro Ile Ile Ile
            580                 585                 590

Glu Asn Lys Asp Glu Phe Gly Ser Glu Leu Ser Arg Asn Met Gln Thr
        595                 600                 605

Ser Glu Thr Asp Ser Leu Val Val Ala Val Glu Glu Asp Val Lys Asn
    610                 615                 620

Asp Glu Val Ala Gln Val Glu Glu Leu Leu Glu Ser Glu Lys Val Glu
625                 630                 635                 640

Asn Gln Ser Ser Glu Leu Leu Ser Asp Thr Leu Ile Val Glu Ser Ala
                645                 650                 655

Asn Asp Lys Glu Glu Asp Arg Val Glu Ala Val Val Ser Glu Gln Pro
            660                 665                 670

Asp Ser Ile Pro His Gln Asn Val Glu Ile Ser Leu Val Glu Pro Thr
        675                 680                 685

Asn Val Glu Thr Glu Thr Val Val Thr Pro Ile Asn Asp Ala Ala Thr
    690                 695                 700

Pro His Gly Ser Pro Thr Tyr Ile Asp Asn Ser Val Thr Glu Ser Val
705                 710                 715                 720

Ala Thr Pro Leu Glu Lys Asp Ser Ile Gln Ala Gly Glu Thr Glu Ile
                725                 730                 735

Ala Glu Pro Thr Ser Ser Glu Ser Thr Asn Val Glu Thr Glu Thr Val
            740                 745                 750

Val Thr Pro Val Asn Asp Val Ala Thr Pro His Gly Ser Pro Thr Tyr
        755                 760                 765

Ile Asp Asn Ser Val Thr Glu Ser Val Ala Thr Pro Leu Glu Lys Asp
    770                 775                 780

Ser Ile Gln Ala Gly Glu Thr Glu Ile Ala Glu Pro Thr Ser Ser Glu
785                 790                 795                 800

Ser Thr Asn Val Glu Thr Glu Thr Val Val Thr Pro Val Asn Asp Val
                805                 810                 815

Ala Thr Pro His Gly Ser Pro Thr Tyr Ile Asp Asn Ser Val Thr Glu
            820                 825                 830

Ser Val Ala Thr Pro Leu Glu Lys Asp Ser Ile Gln Ala Gly Glu Thr
        835                 840                 845

Glu Ile Ala Glu Pro Thr Ser Ser Glu Ser Thr Ser Val Glu Ala Glu
    850                 855                 860

Leu Val Asp Asn Ser Glu Ile His Ala Ala Thr Ser Ser Val Thr Pro
865                 870                 875                 880

Cys Gly Ser Ser Ala Tyr Ala Asp Gly Ser Thr Thr Glu Ser Val Ala
                885                 890                 895

Thr Pro Leu Glu Lys Asp Ser Ile Gln Thr Gly Asn Thr Glu Ile Ala
            900                 905                 910

Glu Pro Thr Ser Ser Lys Ser Thr Asn Val Glu Ala Ala Ser Val Asp
        915                 920                 925

Asn Ser Glu Ile His Ala Asp Ala Ser Leu Thr Ala Val Ser Ser Val
    930                 935                 940

Asn Leu Asp Asn Pro Val Ile Glu Pro Val Ala Ile Ser Leu Ile Gly
945                 950                 955                 960

Ser Lys Arg Asp Thr Asn Ala Glu Val Glu Val Ser Ser Leu Ser Lys
                965                 970                 975

Arg Glu Val Arg Lys Thr Asn Thr Asp Gly Leu Ile Ser Val Gln Ser
```

-continued

```
            980                 985                 990

Lys Val Ile Lys Lys Glu Leu Leu  Glu Ser Ser Leu Ala  Glu Ala Gly
        995                 1000                1005

Ser Pro  Leu Leu Glu Ala Thr  Ile Ala Gln Ser Ser  Asn Ser Asn
    1010                 1015                 1020

Ser Thr  Glu Ile Gly Met Ser  Tyr Gln Asn Thr Val  Leu Leu Glu
    1025                 1030                 1035

Ser Asn  Asn Thr Glu Arg Gln  Val Ser Lys Ala Glu  Ile Val Met
    1040                 1045                 1050

Glu His  Lys Glu Thr Glu Leu  Val Glu Thr Val Ser  Ser Ala Ser
    1055                 1060                 1065

Glu Pro  Val Val Leu Val Glu  Asn Ile Ser Gln Thr  Ser Asn Asn
    1070                 1075                 1080

Thr Ile  Glu Ser Gly Lys Asn  Met Gly Val Gln Ser  Gln Ala Gly
    1085                 1090                 1095

Ala Lys  Gln Ile Leu Gly Val  Glu Gln Ser Ser Lys  Val Ser Thr
    1100                 1105                 1110

Pro Thr  Ser Arg Gln Ile Met  Gly Val Gly Leu Leu  Thr Leu Val
    1115                 1120                 1125

Leu Gly  Ser Ala Leu Gly Leu  Leu Lys Lys Arg Arg  Lys
    1130                 1135                 1140


<210> SEQ ID NO 2
<211> LENGTH: 1130
<212> TYPE: PRT
<213> ORGANISM: Artificial sequence
<220> FEATURE:
<223> OTHER INFORMATION: Artificial rIdeSsuis protein sequence

<400> SEQUENCE: 2

Met Ala His His His His His His Val Gly Thr Gly Ser Asn Asp Asp
1               5                   10                  15

Asp Asp Lys Ser Pro Asp Pro Val Val Thr Gly Val Asn Glu Ile Ile
            20                  25                  30

Glu Glu Ser Gln Val Lys Asp Glu Val Ser Ile Glu Ser Glu Lys Asn
        35                  40                  45

Glu Ser Leu Asp Gly Ser Asn Ile Glu Ile Val Glu Glu Ile Ala Asp
    50                  55                  60

Asn Ile Pro Ser Pro Val Ile Ala Glu Gly Glu Val Ala Val Glu Met
65                  70                  75                  80

Lys Val Asp Arg Gly Thr Glu Asn Val Val Ser Arg Asn Asp Thr Glu
                85                  90                  95

Val Thr Thr Ser Glu Gln Asn Gln Ile Glu Val Thr Glu Thr Lys Glu
            100                 105                 110

Ile Leu Asn Gln Thr Ser Tyr Gln Thr Glu Ser Gly Glu Gln Arg Gln
        115                 120                 125

Ile Ile Trp Ala His Gly Ile Thr Pro Pro Ala Met Glu Gln Ser Gly
    130                 135                 140

Gly Phe Val Lys Glu Lys Tyr Gly Asp Tyr Leu Asn Tyr Thr Ala Pro
145                 150                 155                 160

Phe Glu Ala Gly Lys Gly Tyr Tyr Asp Thr Asn Lys Ser Leu Asn Ala
                165                 170                 175

Ser Phe Ile Asp Leu Asn Leu Cys Phe Ala Ala Val Ser Ser Asn Met
            180                 185                 190

Val His Trp Trp Leu Glu Gln Asn Ser Ser Tyr Val Glu Arg Tyr Leu
```

-continued

```
        195                 200                 205

Lys Glu Lys Lys Gly Thr Val Asn Val Glu Glu Asn Tyr Ala Ile Thr
    210                 215                 220

Asp Leu Arg Arg Tyr Ile Asn Ser Phe Gln Asn Gln Gln Asn Ser Arg
225                 230                 235                 240

Val Phe Asp Met Phe Lys Thr Tyr Tyr Gly Tyr Arg Thr Asn Gly Phe
                245                 250                 255

Val Ser Asp Ala Leu Val Asp Leu Phe Ile Asn Gly Tyr Lys Pro Lys
            260                 265                 270

Ala Gln Gly Gly Val Asn Leu Glu Asp Ser Gln Leu Val Pro Asp Ser
        275                 280                 285

Arg Gly Gly Phe Phe Tyr Asp Val Phe Lys Glu Lys Lys Leu Thr Asn
    290                 295                 300

Arg Ile Phe Ser Gly Ser Tyr Glu Arg Phe Gly Glu Asp Val Arg Thr
305                 310                 315                 320

Val Leu Glu Ser Lys Gly Leu Leu Gly Leu Thr Tyr Arg Thr Leu Gly
                325                 330                 335

Tyr Ala Thr His Ile Val Thr Val Trp Gly Ala Glu Tyr Asp Asn Gln
            340                 345                 350

Gly Lys Ile Lys Ala Val Tyr Ile Thr Asp Ser Asp Asp Gln Gln Glu
        355                 360                 365

Gln Ile Gly Leu Lys Arg Met Gly Ile Thr Arg Asp Ala Ser Gly Asn
    370                 375                 380

Pro Arg Leu Asn Asn His Met Lys Asn Asn Ser Ala Gly Ala Leu Leu
385                 390                 395                 400

Asp Tyr Val His Thr Ile Arg Leu Gly Gln Asp Leu Trp Glu Glu Tyr
                405                 410                 415

Phe Asn Pro Leu Ala Lys Ala Lys Glu Thr Ala Ser Gln Thr Leu Ala
            420                 425                 430

Asp Thr Lys Lys Ala Leu Asp Leu Ser Ile Gln Gly Gln Ser Glu Leu
        435                 440                 445

Pro Glu Ser Met Arg Leu Ile Tyr Leu Glu Lys Leu Asn Asn Leu Tyr
    450                 455                 460

Asn Gln Gly Ile Leu Ser Ile Gln Lys Ala Glu Ser Ser Glu Met Leu
465                 470                 475                 480

Ser Gly Ala Leu Glu Asn Gly Leu Asn Ser Leu Lys Ser Leu Asp Phe
                485                 490                 495

Pro Ile Ser Glu Val Gly Asn Ala Leu Ala Pro Asp Leu Pro Val Gly
            500                 505                 510

Asp Arg Ser Thr Val Ser Asp Val Asp Ser Leu Ser Ser Gln Glu Thr
        515                 520                 525

Ser Ser Thr Asn Leu Glu Ala Asp Thr Glu Asn Ala Gly Ile Ile Ala
    530                 535                 540

Asp Gly Thr Asn Gln Leu His Phe Pro Val Glu Ala Gln Thr Thr Ser
545                 550                 555                 560

Ser Val Glu Ala Glu Gly Asp Asn Val Phe Glu Gln Glu Ala Asp Thr
                565                 570                 575

Leu Pro Ile Ile Ile Glu Asn Lys Asp Glu Phe Gly Ser Glu Leu Ser
            580                 585                 590

Arg Asn Met Gln Thr Ser Glu Thr Asp Ser Leu Val Val Ala Val Glu
        595                 600                 605

Glu Asp Val Lys Asn Asp Glu Val Ala Gln Val Glu Glu Leu Leu Glu
    610                 615                 620
```

-continued

```
Ser Glu Lys Val Glu Asn Gln Ser Ser Glu Leu Leu Ser Asp Thr Leu
625                 630                 635                 640

Ile Val Glu Ser Ala Asn Asp Lys Glu Glu Asp Arg Val Glu Ala Val
                645                 650                 655

Val Ser Glu Gln Pro Asp Ser Ile Pro His Gln Asn Val Glu Ile Ser
            660                 665                 670

Leu Val Glu Pro Thr Asn Val Glu Thr Glu Thr Val Val Thr Pro Ile
        675                 680                 685

Asn Asp Ala Ala Thr Pro His Gly Ser Pro Thr Tyr Ile Asp Asn Ser
    690                 695                 700

Val Thr Glu Ser Val Ala Thr Pro Leu Glu Lys Asp Ser Ile Gln Ala
705                 710                 715                 720

Gly Glu Thr Glu Ile Ala Glu Pro Thr Ser Ser Glu Ser Thr Asn Val
                725                 730                 735

Glu Thr Glu Thr Val Val Thr Pro Val Asn Asp Val Ala Thr Pro His
            740                 745                 750

Gly Ser Pro Thr Tyr Ile Asp Asn Ser Val Thr Glu Ser Val Ala Thr
        755                 760                 765

Pro Leu Glu Lys Asp Ser Ile Gln Ala Gly Glu Thr Glu Ile Ala Glu
    770                 775                 780

Pro Thr Ser Ser Glu Ser Thr Asn Val Glu Thr Glu Thr Val Val Thr
785                 790                 795                 800

Pro Val Asn Asp Val Ala Thr Pro His Gly Ser Pro Thr Tyr Ile Asp
                805                 810                 815

Asn Ser Val Thr Glu Ser Val Ala Thr Pro Leu Glu Lys Asp Ser Ile
            820                 825                 830

Gln Ala Gly Glu Thr Glu Ile Ala Glu Pro Thr Ser Ser Glu Ser Thr
        835                 840                 845

Ser Val Glu Ala Glu Leu Val Asp Asn Ser Glu Ile His Ala Ala Thr
    850                 855                 860

Ser Ser Val Thr Pro Cys Gly Ser Ser Ala Tyr Ala Asp Gly Ser Thr
865                 870                 875                 880

Thr Glu Ser Val Ala Thr Pro Leu Glu Lys Asp Ser Ile Gln Thr Gly
                885                 890                 895

Asn Thr Glu Ile Ala Glu Pro Thr Ser Ser Lys Ser Thr Asn Val Glu
            900                 905                 910

Ala Ala Ser Val Asp Asn Ser Glu Ile His Ala Asp Ala Ser Leu Thr
        915                 920                 925

Ala Val Ser Ser Val Asn Leu Asp Asn Pro Val Ile Glu Pro Val Ala
    930                 935                 940

Ile Ser Leu Ile Gly Ser Lys Arg Asp Thr Asn Ala Glu Val Glu Val
945                 950                 955                 960

Ser Ser Leu Ser Lys Arg Glu Val Arg Lys Thr Asn Thr Asp Gly Leu
                965                 970                 975

Ile Ser Val Gln Ser Lys Val Ile Lys Lys Glu Leu Leu Glu Ser Ser
            980                 985                 990

Leu Ala Glu Ala Gly Ser Pro Leu  Leu Glu Ala Thr Ile  Ala Gln Ser
        995                 1000                1005

Ser Asn  Ser Asn Ser Thr Glu  Ile Gly Met Ser Tyr  Gln Asn Thr
    1010                1015                1020

Val Leu  Leu Glu Ser Asn Asn  Thr Glu Arg Gln Val  Ser Lys Ala
    1025                1030                1035
```

-continued

```
Glu Ile  Val Met Glu His Lys  Glu Thr Glu Leu Val  Glu Thr Val
    1040                1045                1050

Ser Ser  Ala Ser Glu Pro Val  Val Leu Val Glu Asn  Ile Ser Gln
    1055                1060                1065

Thr Ser  Asn Asn Thr Ile Glu  Ser Gly Lys Asn Met  Gly Val Gln
    1070                1075                1080

Ser Gln  Ala Gly Ala Lys Gln  Ile Leu Gly Val Glu  Gln Ser Ser
    1085                1090                1095

Lys Val  Ser Thr Pro Thr Ser  Arg Gln Ile Met Gly  Val Gly Leu
    1100                1105                1110

Leu Thr  Leu Val Leu Gly Ser  Ala Leu Gly Leu Leu  Lys Lys Arg
    1115                1120                1125

Arg Lys
    1130


<210> SEQ ID NO 3
<211> LENGTH: 3426
<212> TYPE: DNA
<213> ORGANISM: Streptococcus suis

<400> SEQUENCE: 3

atgaacattc aagaacgatt ttctttgaga aaatccgcgg ttggcttggt ctcagtctct     60

ttgctatgtg ctatttatac atccactgtt gctgccgata cagttgttac aggagtgaat    120

gaaataattg aagaatcaca agtcaaggat gaggtatcta ttgaatcaga aaaaaatgaa    180

tccctagatg gttctaatat tgaaattgta gaggaaatag cagacaacat cccatcacct    240

gttatcgctg aaggggaagt agcggtagag atgaaagttg acagagggac cgagaatgta    300

gtttctagaa atgatacaga agttacgacg agcgagcaaa atcagataga ggttactgag    360

acaaaagaaa ttttgaatca gaccagttat caaacggaga gtggcgagca acgacaaatt    420

atatgggccc atggaattac tcctcctgca atggaacaaa gcggtggttt tgtaaaggaa    480

aagtatggag actatttaaa ctatacagcg ccatttgagg ctggaaaagg ctactatgat    540

accaataaga gtctgaatgc ttcatttatt gaccttaatc tttgttttgc agctgtgtct    600

tcaaacatgg tacattggtg gttggaacag aatagttcct atgttgagcg atatctcaaa    660

gaaaaaaagg gtacagtaaa tgttgaagaa aactacgcaa taacggactt acggcgctat    720

attaattcat tccaaaatca acaaaatagt cgagtttttg atatgttcaa aacttactat    780

ggttatcgta caaatggttt tgtatcagat gccttggttg acttgtttat taacggatat    840

aaacctaagg cacagggcgg tgtcaatctg gaagatagcc agttagtacc agatagtagg    900

ggtggctttt tctacgacgt tttcaaagag aaaaaactga caaatcgaat ttttagtggt    960

agttatgagc ggtttggtga ggatgttcga actgttttgg aaagcaaagg attactcggc   1020

ttaacttata gaacattagg ttatgcaacg catattgtga cggtatgggg tgctgagtac   1080

gacaatcaag gtaagattaa ggctgtctat atcacagatt ctgatgatca acaagaacaa   1140

attggtttga agcgtatggg aatcactcgt gatgcttccg gaaatccacg tttgaataat   1200

catatgaaaa ataattcagc tggagcgctt ttggattatg tccatacaat ccgtctgggt   1260

caagacttat gggaagaata tttcaatccg cttgcaaaag ccaaagaaac agctagtcag   1320

acattagccg atacaaagaa ggcgttggat ttgtctattc aaggacaatc tgaattgcca   1380

gaatcaatgc gactgattta tcttgaaaaa ctaaataatc tctataatca aggaattcta   1440

tctattcaaa aggcagaaag ttctgagatg ctaagtggtg cattggaaaa tggtttaaat   1500
```

-continued

```
agtttaaaga gtttagattt tcctatttca gaagttggaa atgctttggc accagattta   1560

ccagtaggtg atcgctcaac ggtttcagat gttgattctc tatcatctca agaaacaagt   1620

tccacaaatt tggaagcaga cacagagaat gcaggtatta ttgcagatgg taccaatcaa   1680

ttgcattttc cagtggaggc ccaaacgaca tcttcagtag aggctgaggg agataatgtt   1740

tttgaacaag aggcagatac attaccaata attattgaaa acaaggatga atttggttca   1800

gaactatcaa gaaacatgca aacgtcagaa acggattcgc tagtagtagc tgttgaagaa   1860

gatgtgaaaa atgatgaggt agcccaagtt gaagagcttc ttgaatcaga aaaagttgaa   1920

aatcagagtt cggaacttct gtcagacacc ctaatcgtag agagtgcaaa tgacaaagaa   1980

gaagatagag tggaggcggt tgtttctgaa caaccagact caataccaca tcaaaatgta   2040

gaaatctctc ttgtagaacc aacgaatgtc gaaactgaaa ctgtggtcac tcctattaat   2100

gatgcagcta ctcctcatgg ttccccgacg tatatagata attccgtaac tgaatctgta   2160

gctactccac ttgaaaaaga ctccattcaa gccggggaga cagagattgc agaaccaacc   2220

tcgagcgaat caacgaatgt cgaaactgaa actgtggtca ctcctgttaa tgatgtagct   2280

actcctcatg gttccccgac gtatatagat aattccgtaa ctgaatctgt agctactcca   2340

cttgaaaaag actccattca agccggagag acagaaattg cagaaccaac ctcgagcgaa   2400

tcaacgaatg tcgaaactga aactgtggtc actcctgtta atgatgtagc tactcctcat   2460

ggttccccga cgtatataga taattccgta actgaatctg tagctactcc acttgaaaaa   2520

gactccattc aagccgggga gacagagatt gcagaaccaa cctcgagcga atcaactagt   2580

gttgaagctg aacttgtcga caattctgaa attcatgcag ctacctcttc agttactccc   2640

tgtggctcct cggcatatgc agatggttcc acaactgaat ctgtagccac tccgcttgaa   2700

aaagactcca ttcagactgg aaatacagaa attgcagaac caacctcgag caaatcaact   2760

aatgtagaag ctgcatctgt cgacaattct gaaattcatg cagatgcctc tctaactgct   2820

gtttcatcag ttaatctgga taatccagtg attgaaccag tagctatctc ccttatcggt   2880

tctaagaggg acacgaatgc agaagtagaa gtttcttcat tatcgaaaag agaggttaga   2940

aaaacaaata ctgacgggct aatctctgtt caatcaaaag ttattaagaa agaattgcta   3000

gaatcaagct tagcagaagc agggtctcca ttgctagaag ccaccattgc tcagtcttca   3060

aactcaaata gtactgagat aggtatgagc tatcagaata ctgtgttatt agagtctaat   3120

aatacagagc gtcaggtgtc taaagcagaa attgttatgg aacacaagga gacagagtta   3180

gttgaaacgg tttcatctgc ttctgagcct gtagtgctcg tagaaaatat ctcacaaacc   3240

tcaaataata ctattgaatc tggtaagaat atgggagttc aatctcaagc aggtgcaaaa   3300

caaattttag gcgtagaaca atcttcgaaa gtaagtacac ctacttcaag acagattatg   3360

ggagtcggtc tattgactct tgttcttggt agtgctttag gtttgttaaa gaaaagacgt   3420

aagtaa                                                              3426
```

```
<210> SEQ ID NO 4
<211> LENGTH: 3393
<212> TYPE: DNA
<213> ORGANISM: Artificial sequence
<220> FEATURE:
<223> OTHER INFORMATION: Artificial nucleotide sequence encoding
      rIdeSsuis

<400> SEQUENCE: 4

atggcacatc accaccacca tcacgtgggt accggttcga atgatgacga cgacaagagt     60
```

-continued

```
ccggatccag ttgttacagg agtgaatgaa ataattgaag aatcacaagt caaggatgag    120
gtatctattg aatcagaaaa aaatgaatcc ctagatggtt ctaatattga aattgtagag    180
gaaatagcag acaacatccc atcacctgtt atcgctgaag gggaagtagc ggtagagatg    240
aaagttgaca gagggaccga gaatgtagtt tctagaaatg atacagaagt tacgacgagc    300
gagcaaaatc agatagaggt tactgagaca aaagaaattt tgaatcagac cagttatcaa    360
acggagagtg gcgagcaacg acaaattata tgggcccatg gaattactcc tcctgcaatg    420
gaacaaagcg gtggttttgt aaaggaaaag tatggagact atttaaacta tacagcgcca    480
tttgaggctg gaaaaggcta ctatgatacc aataagagtc tgaatgcttc atttattgac    540
cttaatcttt gttttgcagc tgtgtcttca aacatggtac attggtggtt ggaacagaat    600
agttcctatg ttgagcgata tctcaaagaa aaaaagggta cagtaaatgt tgaagaaaac    660
tacgcaataa cggacttacg gcgctatatt aattcattcc aaaatcaaca aaatagtcga    720
gtttttgata tgttcaaaac ttactatggt tatcgtacaa atggttttgt atcagatgcc    780
ttggttgact tgtttattaa cggatataaa cctaaggcac agggcggtgt caatctggaa    840
gatagccagt tagtaccaga tagtaggggt ggctttttct acgacgtttt caaagagaaa    900
aaactgacaa atcgaatttt tagtggtagt tatgagcggt ttggtgagga tgttcgaact    960
gttttggaaa gcaaaggatt actcggctta acttatagaa cattaggtta tgcaacgcat   1020
attgtgacgg tatggggtgc tgagtacgac aatcaaggta agattaaggc tgtctatatc   1080
acagattctg atgatcaaca agaacaaatt ggtttgaagc gtatgggaat cactcgtgat   1140
gcttccggaa atccacgttt gaataatcat atgaaaaata attcagctgg agcgcttttg   1200
gattatgtcc atacaatccg tctgggtcaa gacttatggg aagaatattt caatccgctt   1260
gcaaaagcca aagaaacagc tagtcagaca ttagccgata caaagaaggc gttggatttg   1320
tctattcaag gacaatctga attgccagaa tcaatgcgac tgatttatct tgaaaaacta   1380
aataatctct ataatcaagg aattctatct attcaaaagg cagaaagttc tgagatgcta   1440
agtggtgcat tggaaaatgg tttaaatagt ttaaagagtt tagattttcc tatttcagaa   1500
gttggaaatg ctttggcacc agatttacca gtaggtgatc gctcaacggt ttcagatgtt   1560
gattctctat catctcaaga aacaagttcc acaaatttgg aagcagacac agagaatgca   1620
ggtattattg cagatggtac caatcaattg cattttccag tggaggccca aacgacatct   1680
tcagtagagg ctgagggaga taatgttttt gaacaagagg cagatacatt accaataatt   1740
attgaaaaca aggatgaatt tggttcagaa ctatcaagaa acatgcaaac gtcagaaacg   1800
gattcgctag tagtagctgt tgaagaagat gtgaaaaatg atgaggtagc ccaagttgaa   1860
gagcttcttg aatcagaaaa agttgaaaat cagagttcgg aacttctgtc agacacccta   1920
atcgtagaga gtgcaaatga caaagaagaa gatagagtgg aggcggttgt ttctgaacaa   1980
ccagactcaa taccacatca aaatgtagaa atctctcttg tagaaccaac gaatgtcgaa   2040
actgaaactg tggtcactcc tattaatgat gcagctactc ctcatggttc cccgacgtat   2100
atagataatt ccgtaactga atctgtagct actccacttg aaaaagactc cattcaagcc   2160
ggggagacag agattgcaga accaacctcg agcgaatcaa cgaatgtcga aactgaaact   2220
gtggtcactc ctgttaatga tgtagctact cctcatggtt ccccgacgta tatagataat   2280
tccgtaactg aatctgtagc tactccactt gaaaaagact ccattcaagc cggagagaca   2340
gaaattgcag aaccaacctc gagcgaatca acgaatgtcg aaactgaaac tgtggtcact   2400
cctgttaatg atgtagctac tcctcatggt tccccgacgt atatagataa ttccgtaact   2460
```

-continued

```
gaatctgtag ctactccact tgaaaaagac tccattcaag ccggggagac agagattgca   2520

gaaccaacct cgagcgaatc aactagtgtt gaagctgaac ttgtcgacaa ttctgaaatt   2580

catgcagcta cctcttcagt tactccctgt ggctcctcgg catatgcaga tggttccaca   2640

actgaatctg tagccactcc gcttgaaaaa gactccattc agactggaaa tacagaaatt   2700

gcagaaccaa cctcgagcaa atcaactaat gtagaagctg catctgtcga caattctgaa   2760

attcatgcag atgcctctct aactgctgtt tcatcagtta atctggataa tccagtgatt   2820

gaaccagtag ctatctccct tatcggttct aagagggaca cgaatgcaga agtagaagtt   2880

tcttcattat cgaaaagaga ggttagaaaa acaaatactg acgggctaat ctctgttcaa   2940

tcaaaagtta ttaagaaaga attgctagaa tcaagcttag cagaagcagg gtctccattg   3000

ctagaagcca ccattgctca gtcttcaaac tcaaatagta ctgagatagg tatgagctat   3060

cagaatactg tgttattaga gtctaataat acagagcgtc aggtgtctaa agcagaaatt   3120

gttatggaac acaaggagac agagttagtt gaaacggttt catctgcttc tgagcctgta   3180

gtgctcgtag aaaatatctc acaaacctca aataatacta ttgaatctgg taagaatatg   3240

ggagttcaat ctcaagcagg tgcaaaacaa attttaggcg tagaacaatc ttcgaaagta   3300

agtacaccta cttcaagaca gattatggga gtcggtctat tgactcttgt tcttggtagt   3360

gctttaggtt tgttaaagaa aagacgtaag taa                                3393
```

```
<210> SEQ ID NO 5
<211> LENGTH: 335
<212> TYPE: PRT
<213> ORGANISM: Artificial sequence
<220> FEATURE:
<223> OTHER INFORMATION: Artificial partial sequence of Mac-1 domain

<400> SEQUENCE: 5

Met Lys Val Asp Arg Gly Thr Glu Asn Val Val Ser Arg Asn Asp Thr
1               5                   10                  15

Glu Val Thr Thr Ser Glu Gln Asn Gln Ile Glu Val Thr Glu Thr Lys
            20                  25                  30

Glu Ile Leu Asn Gln Thr Ser Tyr Gln Thr Glu Ser Gly Glu Gln Arg
        35                  40                  45

Gln Ile Ile Trp Ala His Gly Ile Thr Pro Pro Ala Met Glu Gln Ser
    50                  55                  60

Gly Gly Phe Val Lys Glu Lys Tyr Gly Asp Tyr Leu Asn Tyr Thr Ala
65                  70                  75                  80

Pro Phe Glu Ala Gly Lys Gly Tyr Tyr Asp Thr Asn Lys Ser Leu Asn
                85                  90                  95

Ala Ser Phe Ile Asp Leu Asn Leu Cys Phe Ala Ala Val Ser Ser Asn
            100                 105                 110

Met Val His Trp Trp Leu Glu Gln Asn Ser Ser Tyr Val Glu Arg Tyr
        115                 120                 125

Leu Lys Glu Lys Lys Gly Thr Val Asn Val Glu Glu Asn Tyr Ala Ile
    130                 135                 140

Thr Asp Leu Arg Arg Tyr Ile Asn Ser Phe Gln Asn Gln Gln Asn Ser
145                 150                 155                 160

Arg Val Phe Asp Met Phe Lys Thr Tyr Tyr Gly Tyr Arg Thr Asn Gly
                165                 170                 175

Phe Val Ser Asp Ala Leu Val Asp Leu Phe Ile Asn Gly Tyr Lys Pro
            180                 185                 190
```

-continued

```
Lys Ala Gln Gly Gly Val Asn Leu Glu Asp Ser Gln Leu Val Pro Asp
        195                 200                 205

Ser Arg Gly Gly Phe Phe Tyr Asp Val Phe Lys Glu Lys Lys Leu Thr
    210                 215                 220

Asn Arg Ile Phe Ser Gly Ser Tyr Glu Arg Phe Gly Glu Asp Val Arg
225                 230                 235                 240

Thr Val Leu Glu Ser Lys Gly Leu Leu Gly Leu Thr Tyr Arg Thr Leu
                245                 250                 255

Gly Tyr Ala Thr His Ile Val Thr Val Trp Gly Ala Glu Tyr Asp Asn
            260                 265                 270

Gln Gly Lys Ile Lys Ala Val Tyr Ile Thr Asp Ser Asp Asp Gln Gln
        275                 280                 285

Glu Gln Ile Gly Leu Lys Arg Met Gly Ile Thr Arg Asp Ala Ser Gly
    290                 295                 300

Asn Pro Arg Leu Asn Asn His Met Lys Asn Asn Ser Ala Gly Ala Leu
305                 310                 315                 320

Leu Asp Tyr Val His Thr Ile Arg Leu Gly Gln Asp Leu Trp Glu
                325                 330                 335


<210> SEQ ID NO 6
<211> LENGTH: 457
<212> TYPE: PRT
<213> ORGANISM: Artificial sequence
<220> FEATURE:
<223> OTHER INFORMATION: Artificial rIdeSsuis_homologue sequence

<400> SEQUENCE: 6

Met Ala His His His His His His Val Gly Thr Gly Ser Asn Asp Asp
1               5                   10                  15

Asp Asp Lys Ser Pro Asp Pro Val Val Thr Gly Val Asn Glu Ile Ile
            20                  25                  30

Glu Glu Ser Gln Val Lys Asp Glu Val Ser Ile Glu Ser Glu Lys Asn
        35                  40                  45

Glu Ser Leu Asp Gly Ser Asn Ile Glu Ile Val Glu Glu Ile Ala Asp
    50                  55                  60

Asn Ile Pro Ser Pro Val Ile Ala Glu Gly Glu Val Ala Val Glu Met
65                  70                  75                  80

Lys Val Asp Arg Gly Thr Glu Asn Val Val Ser Arg Asn Asp Thr Glu
                85                  90                  95

Val Thr Thr Ser Glu Gln Asn Gln Ile Glu Val Thr Glu Thr Lys Glu
            100                 105                 110

Ile Leu Asn Gln Thr Ser Tyr Gln Thr Glu Ser Gly Glu Gln Arg Gln
        115                 120                 125

Ile Ile Trp Ala His Gly Ile Thr Pro Pro Ala Met Glu Gln Ser Gly
    130                 135                 140

Gly Phe Val Lys Glu Lys Tyr Gly Asp Tyr Leu Asn Tyr Thr Ala Pro
145                 150                 155                 160

Phe Glu Ala Gly Lys Gly Tyr Tyr Asp Thr Asn Lys Ser Leu Asn Ala
                165                 170                 175

Ser Phe Ile Asp Leu Asn Leu Cys Phe Ala Ala Val Ser Ser Asn Met
            180                 185                 190

Val His Trp Trp Leu Glu Gln Asn Ser Ser Tyr Val Glu Arg Tyr Leu
        195                 200                 205

Lys Glu Lys Lys Gly Thr Val Asn Val Glu Glu Asn Tyr Ala Ile Thr
    210                 215                 220
```

-continued

```
Asp Leu Arg Arg Tyr Ile Asn Ser Phe Gln Asn Gln Gln Asn Ser Arg
225                 230                 235                 240

Val Phe Asp Met Phe Lys Thr Tyr Tyr Gly Tyr Arg Thr Asn Gly Phe
                245                 250                 255

Val Ser Asp Ala Leu Val Asp Leu Phe Ile Asn Gly Tyr Lys Pro Lys
            260                 265                 270

Ala Gln Gly Gly Val Asn Leu Glu Asp Ser Gln Leu Val Pro Asp Ser
        275                 280                 285

Arg Gly Gly Phe Phe Tyr Asp Val Phe Lys Glu Lys Lys Leu Thr Asn
    290                 295                 300

Arg Ile Phe Ser Gly Ser Tyr Glu Arg Phe Gly Glu Asp Val Arg Thr
305                 310                 315                 320

Val Leu Glu Ser Lys Gly Leu Leu Gly Leu Thr Tyr Arg Thr Leu Gly
                325                 330                 335

Tyr Ala Thr His Ile Val Thr Val Trp Gly Ala Glu Tyr Asp Asn Gln
            340                 345                 350

Gly Lys Ile Lys Ala Val Tyr Ile Thr Asp Ser Asp Asp Gln Gln Glu
        355                 360                 365

Gln Ile Gly Leu Lys Arg Met Gly Ile Thr Arg Asp Ala Ser Gly Asn
    370                 375                 380

Pro Arg Leu Asn Asn His Met Lys Asn Asn Ser Ala Gly Ala Leu Leu
385                 390                 395                 400

Asp Tyr Val His Thr Ile Arg Leu Gly Gln Asp Leu Trp Glu Glu Tyr
                405                 410                 415

Phe Asn Pro Leu Ala Lys Ala Cys Arg Ser Thr Ser Leu Arg Pro His
            420                 425                 430

Ser Ser Leu Val Lys Lys Pro Leu Leu Arg Asn Leu Asn Ala Ser Thr
        435                 440                 445

Trp Thr Arg Leu Leu Ala Gln Leu Asn
    450                 455


<210> SEQ ID NO 7
<211> LENGTH: 1016
<212> TYPE: PRT
<213> ORGANISM: Artificial sequence
<220> FEATURE:
<223> OTHER INFORMATION: Artificial rIdeSsuisB2 sequence

<400> SEQUENCE: 7

Met Ala His His His His His His Val Gly Thr Gly Ser Asn Asp Asp
1               5                   10                  15

Asp Asp Lys Ser Pro Asp Pro Val Val Thr Gly Val Asn Glu Ile Ile
            20                  25                  30

Glu Glu Ser Gln Val Lys Asp Glu Val Ser Ile Glu Ser Glu Lys Asn
        35                  40                  45

Glu Ser Leu Asp Gly Ser Asn Ile Glu Ile Val Glu Glu Ile Ala Asp
    50                  55                  60

Asn Ile Pro Ser Pro Val Ile Ala Glu Gly Glu Val Ala Val Glu Met
65                  70                  75                  80

Lys Val Asp Arg Gly Thr Glu Asn Val Val Ser Arg Asn Asp Thr Glu
                85                  90                  95

Val Thr Thr Ser Glu Gln Asn Gln Ile Glu Val Thr Glu Thr Lys Glu
            100                 105                 110

Ile Leu Asn Gln Thr Ser Tyr Gln Thr Glu Ser Gly Glu Gln Arg Gln
        115                 120                 125
```

```
Ile Ile Trp Ala His Gly Ile Thr Pro Pro Ala Met Glu Gln Ser Gly
    130                 135                 140

Gly Phe Val Lys Glu Lys Tyr Gly Asp Tyr Leu Asn Tyr Thr Ala Pro
145                 150                 155                 160

Phe Lys Ala Gly Lys Gly Tyr Tyr Asp Thr Asn Lys Ser Leu Asn Ala
                165                 170                 175

Ser Phe Ile Asp Leu Asn Leu Cys Phe Ala Ala Val Ser Ser Asn Met
            180                 185                 190

Val His Trp Trp Leu Glu Gln Asn Ser Ser Tyr Val Glu Arg Tyr Leu
        195                 200                 205

Lys Glu Lys Lys Gly Thr Val Asn Val Gly Glu Asn Tyr Ala Ile Thr
    210                 215                 220

Asp Leu Arg Arg Tyr Ile Asp Ser Phe Gln Asp Gln Gln Asn Ser Arg
225                 230                 235                 240

Val Phe Asp Met Phe Lys Thr Tyr Tyr Gly Tyr Arg Thr Asn Gly Phe
                245                 250                 255

Val Ser Asp Ala Leu Val Asp Leu Phe Ile Asn Gly Tyr Lys Pro Lys
            260                 265                 270

Val Gln Gly Gly Val Asn Leu Glu Asp Ser Gln Leu Val Pro Asp Ser
        275                 280                 285

Arg Gly Gly Phe Phe Tyr Asp Val Phe Lys Glu Lys Lys Leu Thr Asn
    290                 295                 300

Arg Ile Phe Ser Gly Ser Tyr Glu Arg Phe Gly Glu Asp Val Arg Thr
305                 310                 315                 320

Val Leu Glu Ser Lys Gly Leu Leu Gly Leu Thr Tyr Arg Thr Leu Gly
                325                 330                 335

Tyr Ala Thr His Ile Val Thr Val Trp Gly Ala Glu Tyr Asp Asn Gln
            340                 345                 350

Gly Lys Ile Arg Ala Val Tyr Ile Thr Asp Ser Asp Asp Gln Gln Glu
        355                 360                 365

Gln Ile Gly Leu Lys Arg Met Gly Ile Thr Arg Asp Ala Ser Gly Asn
    370                 375                 380

Pro Arg Leu Asn Asn His Val Lys Asn Asn Ser Ala Gly Ala Leu Leu
385                 390                 395                 400

Asp Tyr Val His Thr Ile Arg Leu Gly Gln Asp Leu Trp Glu Glu Tyr
                405                 410                 415

Phe Asn Pro Phe Ala Lys Ala Lys Glu Ile Ala Ser Gln Ile Leu Ala
            420                 425                 430

Asp Arg Lys Lys Ala Leu Val Leu Ser Ile Gln Gly Gln Ser Glu Leu
        435                 440                 445

Pro Glu Ser Met Arg Leu Ile Tyr Leu Glu Lys Leu Asn Asn Leu Tyr
    450                 455                 460

Asn Gln Gly Ile Leu Ser Ile Gln Lys Thr Glu Ser Ser Glu Met Leu
465                 470                 475                 480

Ser Gly Ala Leu Glu Asn Gly Leu Asn Ser Leu Lys Ser Leu Asp Phe
                485                 490                 495

Pro Ile Ser Glu Val Gly Asn Ala Leu Ala Pro Asp Leu Ser Val Gly
            500                 505                 510

Asp Arg Ser Thr Val Ser Asp Val Asp Ser Leu Ser Ser Gln Glu Thr
        515                 520                 525

Ser Ser Thr Asn Leu Glu Ala Asp Thr Glu Asn Ala Gly Ile Ile Ala
    530                 535                 540

Asp Gly Thr Asn Gln Leu His Phe Pro Val Glu Ala Gln Thr Thr Ser
```

-continued

```
545                 550                 555                 560

Ser Val Glu Ala Glu Gly Asp Asn Val Phe Glu Gln Glu Ala Asp Thr
                565                 570                 575

Leu Pro Ile Ile Ile Glu Asn Lys Asp Glu Phe Gly Ser Glu Leu Ser
            580                 585                 590

Gly Asn Met Gln Thr Ser Glu Thr Asp Ser Leu Val Val Ala Val Glu
        595                 600                 605

Glu Asp Val Lys Asn Asp Glu Val Asp Gln Val Glu Lys Leu Leu Glu
    610                 615                 620

Ser Glu Lys Val Glu Asn Gln Ser Ser Glu Leu Leu Ser Asp Thr Leu
625                 630                 635                 640

Ile Val Glu Gly Ala Asn Asp Lys Glu Glu Asp Arg Val Glu Ala Val
                645                 650                 655

Val Ser Glu Gln Pro Asp Ser Ile Pro His Gln Asn Val Glu Ile Ser
            660                 665                 670

Pro Val Glu Pro Met Asn Val Glu Thr Glu Ser Val Val Thr Pro Ile
        675                 680                 685

Asn Asp Ala Ala Thr Pro His Gly Phe Pro Met Tyr Ile Asp Asn Ser
    690                 695                 700

Val Thr Glu Ser Val Ala Thr Pro Leu Glu Lys Asp Ser Ile Gln Ala
705                 710                 715                 720

Gly Glu Thr Glu Ile Ala Glu Pro Thr Ser Ser Glu Ser Thr Ser Val
                725                 730                 735

Glu Ala Glu Leu Val Asp Asn Ser Glu Ile His Ser Ala Thr Ser Ser
            740                 745                 750

Val Thr Pro Arg Gly Ser Ser Ala Tyr Ala Asp Ser Ser Thr Thr Glu
        755                 760                 765

Ser Val Ala Thr Leu Leu Glu Lys Asp Ser Ile Gln Ala Gly Glu Thr
    770                 775                 780

Glu Ile Ala Glu Pro Thr Ser Ser Lys Ser Thr Asn Val Glu Ala Ala
785                 790                 795                 800

Ser Val Asp Asn Ser Glu Ile His Ala Asp Thr Ser Leu Thr Ala Val
                805                 810                 815

Ser Ser Val Asn Leu Asp Asn Pro Val Ile Glu Pro Val Ala Ile Pro
            820                 825                 830

Leu Ile Gly Ser Lys Arg Asp Thr Asn Ala Glu Val Glu Val Ser Ser
        835                 840                 845

Leu Ser Lys Arg Glu Val Arg Lys Pro Asn Thr Glu Gly Leu Ile Ser
    850                 855                 860

Val Gln Ser Lys Val Ile Lys Lys Glu Leu Leu Glu Ser Ser Leu Val
865                 870                 875                 880

Glu Ala Gly Ser Pro Leu Leu Glu Ala Thr Ile Ala Gln Ser Ser Asn
                885                 890                 895

Ser Asn Ser Thr Glu Ile Gly Met Ser Tyr Gln Asn Thr Val Leu Leu
            900                 905                 910

Glu Ser Asn Asn Thr Glu Arg Gln Val Ser Lys Ala Glu Ile Val Ile
        915                 920                 925

Glu His Lys Glu Thr Glu Leu Val Glu Thr Val Ser Ser Ala Ser Glu
    930                 935                 940

Pro Val Val Leu Val Glu Asn Ile Ser Gln Thr Ser Asn Asn Thr Ile
945                 950                 955                 960

Glu Ser Gly Lys Asn Met Gly Val Gln Ser Gln Ala Gly Ala Lys Gln
                965                 970                 975
```

-continued

```
Ile Leu Gly Ile Glu Gln Ser Ser Lys Val Ser Thr Pro Thr Ser Arg
            980                 985                 990

Gln Ile Met Gly Val Gly Leu Leu  Thr Leu Val Leu Gly  Ser Ala Leu
        995                 1000                 1005

Gly Leu  Leu Lys Lys Arg Arg  Lys
    1010                 1015
```

<210> SEQ ID NO 8
<211> LENGTH: 1374
<212> TYPE: DNA
<213> ORGANISM: Artificial sequence
<220> FEATURE:
<223> OTHER INFORMATION: Artificial nucleotide sequence encoding rIdeSsuis_homologue

<400> SEQUENCE: 8

```
atggcacatc accaccacca tcacgtgggt accggttcga atgatgacga cgacaagagt      60

ccggatccag ttgttacagg agtgaatgaa ataattgaag aatcacaagt caaggatgag     120

gtatctattg aatcagaaaa aaatgaatcc ctagatggtt ctaatattga aattgtagag     180

gaaatagcag acaacatccc atcacctgtt atcgctgaag gggaagtagc ggtagagatg     240

aaagttgaca gagggaccga gaatgtagtt tctagaaatg atacagaagt tacgacgagc     300

gagcaaaatc agatagaggt tactgagaca aaagaaattt tgaatcagac cagttatcaa     360

acggagagtg gcgagcaacg acaaattata tgggcccatg gaattactcc tcctgcaatg     420

gaacaaagcg gtggttttgt aaaggaaaag tatggagact atttaaacta tacagcgcca     480

tttgaggctg gaaaaggcta ctatgatacc aataagagtc tgaatgcttc atttattgac     540

cttaatcttt gttttgcagc tgtgtcttca aacatggtac attggtggtt ggaacagaat     600

agttcctatg ttgagcgata tctcaaagaa aaaaagggta cagtaaatgt tgaagaaaac     660

tacgcaataa cggacttacg gcgctatatt aattcattcc aaaatcaaca aaatagtcga     720

gtttttgata tgttcaaaac ttactatggt tatcgtacaa atggttttgt atcagatgcc     780

ttggttgact tgtttattaa cggatataaa cctaaggcac agggcggtgt caatctggaa     840

gatagccagt tagtaccaga tagtaggggt ggctttttct acgacgtttt caaagagaaa     900

aaactgacaa atcgaatttt tagtggtagt tatgagcggt ttggtgagga tgttcgaact     960

gttttggaaa gcaaaggatt actcggctta acttatagaa cattaggtta tgcaacgcat    1020

attgtgacgg tatggggtgc tgagtacgac aatcaaggta agattaaggc tgtctatatc    1080

acagattctg atgatcaaca agaacaaatt ggtttgaagc gtatgggaat cactcgtgat    1140

gcttccggaa atccacgttt gaataatcat atgaaaaata attcagctgg agcgcttttg    1200

gattatgtcc atacaatccg tctgggtcaa gacttatggg aagaatattt caatccgctt    1260

gcaaaagcct gcaggtcgac aagcttgcgg ccgcactcga gtctggtaaa gaaaccgctg    1320

ctgcgaaatt tgaacgccag cacatggact cgtctactag cgcagcttaa ttaa          1374
```

<210> SEQ ID NO 9
<211> LENGTH: 3051
<212> TYPE: DNA
<213> ORGANISM: Artificial sequence
<220> FEATURE:
<223> OTHER INFORMATION: Artificial nucleotide sequence encoding rIdeSsuisB2

<400> SEQUENCE: 9

```
atggcacatc accaccacca tcacgtgggt accggttcga atgatgacga cgacaagagt      60
```

-continued

```
ccggatccag ttgttacagg agtgaatgaa ataattgaag aatcacaagt caaggatgag    120
gtatctattg aatcagaaaa aaatgaatcc ctagatggtt ctaatattga aattgtagag    180
gaaatagcag acaacatccc atcacctgtt atcgctgaag gggaagtagc ggtagagatg    240
aaagttgaca gagggaccga gaatgtagtt tctagaaatg atacagaagt tacgacgagc    300
gagcaaaatc agatagaggt tactgagaca aaagaaattt tgaatcagac cagttatcaa    360
acggagagtg gcgagcaacg acaaattata tgggcccatg gaattactcc tcctgcaatg    420
gaacaaagcg gtggttttgt aaaggaaaag tatggagact atttaaacta tacagcgcca    480
tttaaggcag gaaaaggcta ttatgatacc aataaaagtc tcaatgcttc atttattgac    540
cttaacctat gttttgcagc cgtgtcttcc aacatggtac attggtggtt ggaacagaat    600
agttcctatg ttgagcgata tctcaaagaa aaaaagggta cagtaaatgt tggggaaaac    660
tatgcaataa cggacctacg tcgctatatt gattcgttcc aggatcagca aaatagtcga    720
gtctttgata tgttcaaaac ttactacggt tatcgtacaa atggttttgt gtcagatgcc    780
ctagttgact tgtttattaa tggatataaa cctaaggtac agggtggtgt caatctggaa    840
gatagccagt tagtaccaga tagtaggggt ggctttttct acgacgtttt caaagagaaa    900
aaactgacaa atcgtatttt tagtggtagc tatgagcgtt ttggtgagga tgttcgaact    960
gttttggaga gcaaaggatt actcggtcta acttatagaa cattaggcta tgcaacgcat   1020
attgtgacgg tatggggtgc tgagtacgat aatcaaggta agattagggc tgtctatatc   1080
actgattccg atgatcaaca agaacaaatt ggtttgaagc gtatgggaat cactcgtgat   1140
gcttctggaa atccgcgttt gaataatcat gtgaaaaata attcagctgg ggcgcttttg   1200
gattatgtcc atacaatccg tcttggtcaa gacttatggg aagaatattt caatccgttc   1260
gcaaaagcca aagaaatagc tagtcagata ctagctgata gaaagaaggc gttggttctg   1320
tctattcaag gacaatctga attgccagaa tcaatgcggc tgatttatct tgaaaaacta   1380
aataatctct ataatcaagg gattctatct attcaaaaga cagaaagttc tgagatgcta   1440
agtggtgcat tggaaaatgg tttaaatagt ttaaagagtt tagattttcc tatttcagaa   1500
gttggaaatg ctttggcacc agatttatca gtaggtgatc gctcaacggt ttcagatgtt   1560
gattctctat catctcaaga aacaagttcc acaaatttgg aagcagacac agagaatgca   1620
ggtattattg cagatggtac caatcaattg cattttccag tggaggccca aacgacatct   1680
tcagtagagg ctgagggaga taatgttttt gaacaagagg cagatacatt accaataatt   1740
attgaaaaca aggatgaatt tggttcagaa ctatcaggaa acatgcaaac gtcagaaacg   1800
gattcgctag tagtagctgt tgaagaagat gtgaaaaatg atgaggtaga ccaagttgaa   1860
aagcttcttg aatcagaaaa agttgaaaat cagagttcgg aacttctgtc agacacccta   1920
atcgtagagg gtgcaaatga caaagaagaa gatagagtgg aggcggttgt ttctgaacaa   1980
ccagactcaa taccacatca aaatgtagaa atctctcctg tagaaccaat gaatgtcgaa   2040
actgaatctg tggtcactcc tattaatgat gcagctactc ctcatggttt cccgatgtat   2100
atagataatt ccgtaactga atctgtagct actccacttg aaaaagactc cattcaagcc   2160
ggagagacag aaattgcaga accaacctcg agcgaatcaa ctagtgttga agctgaactt   2220
gtcgacaatt ctgaaatcca ttcagctacc tcttcagtta ctccccgtgg ttcctcggca   2280
tatgcagata gttccacaac tgaatctgta gctactctgc ttgaaaaaga ctccattcag   2340
gctggagaga cagaaattgc agaaccaacc tcgagcaaat caactaatgt cgaagctgca   2400
```

-continued

```
tctgtcgaca attctgaaat tcatgcagat acctctctaa ctgctgtttc atcagtcaat   2460

ctggataatc cagtgattga accagtagct atccccctta tcggttctaa gagggacacg   2520

aatgcagaag tggaagtttc ttcattatcg aaaagagagg ttagaaaacc aaatactgaa   2580

gggctaatct ctgttcaatc aaaagttatt aagaaagaat tgctagaatc aagcttagta   2640

gaagcagggt ctccattgct agaagccacc attgctcagt cttcaaactc aaatagtact   2700

gagataggta tgagctatca gaatactgtg ttattagagt ctaataatac agagcgtcag   2760

gtgtctaaag cagaaattgt tatagaacac aaggagacag agttagttga aacggtttca   2820

tctgcttctg agcctgtagt gctcgtagaa aatatctcac aaacctcaaa taatactatt   2880

gaatctggta agaatatggg agttcaatct caagcaggtg caaaacaaat tttaggcata   2940

gaacaatctt cgaaagtaag tacacctact tcaagacaga ttatgggagt cggtctattg   3000

actcttgttc ttggtagtgc tttaggtttg ttaaagaaaa gacgtaagta a            3051
```

<210> SEQ ID NO 10
<211> LENGTH: 335
<212> TYPE: PRT
<213> ORGANISM: Artificial sequence
<220> FEATURE:
<223> OTHER INFORMATION: amino acids 91 to 425 of WP_044671938

<400> SEQUENCE: 10

```
Met Lys Val Asp Arg Gly Thr Glu Asn Val Val Ser Arg Asn Asp Thr
1               5                   10                  15

Glu Val Thr Thr Ser Glu Gln Asn Gln Ile Glu Val Thr Glu Thr Lys
            20                  25                  30

Glu Ile Leu Asn Gln Thr Ser Tyr Gln Thr Glu Ser Gly Glu Gln Arg
        35                  40                  45

Gln Ile Ile Trp Ala His Gly Ile Thr Pro Pro Ala Met Glu Gln Ser
    50                  55                  60

Gly Gly Phe Val Lys Glu Lys Tyr Gly Asp Tyr Leu Asn Tyr Thr Ala
65                  70                  75                  80

Pro Phe Lys Ala Gly Lys Gly Tyr Tyr Asp Thr Asn Lys Ser Leu Asn
                85                  90                  95

Ala Ser Phe Ile Asp Leu Asn Leu Cys Phe Ala Ala Val Ser Ser Asn
            100                 105                 110

Met Val His Trp Trp Leu Glu Gln Asn Ser Ser Tyr Val Glu Arg Tyr
        115                 120                 125

Leu Lys Glu Lys Lys Gly Thr Val Asn Val Gly Glu Asn Tyr Ala Ile
    130                 135                 140

Thr Asp Leu Arg Arg Tyr Ile Asp Ser Phe Gln Asp Gln Gln Asn Ser
145                 150                 155                 160

Arg Val Phe Asp Met Phe Lys Thr Tyr Tyr Gly Tyr Arg Thr Asn Gly
                165                 170                 175

Phe Val Ser Asp Ala Leu Val Asp Leu Phe Ile Asn Gly Tyr Lys Pro
            180                 185                 190

Lys Val Gln Gly Gly Val Asn Leu Glu Asp Ser Gln Leu Val Pro Asp
        195                 200                 205

Ser Arg Gly Gly Phe Phe Tyr Asp Val Phe Lys Glu Lys Lys Leu Thr
    210                 215                 220

Asn Arg Ile Phe Ser Gly Ser Tyr Glu Arg Phe Gly Glu Asp Val Arg
225                 230                 235                 240

Thr Val Leu Glu Ser Lys Gly Leu Leu Gly Leu Thr Tyr Arg Thr Leu
                245                 250                 255
```

-continued

Gly Tyr Ala Thr His Ile Val Thr Val Trp Gly Ala Glu Tyr Asp Asn
260 265 270

Gln Gly Lys Ile Lys Ala Val Tyr Ile Thr Asp Ser Asp Asp Gln Gln
275 280 285

Glu Gln Ile Gly Leu Lys Arg Met Gly Ile Thr Arg Asp Ala Ser Gly
290 295 300

Asn Pro Arg Leu Asn Asn His Met Lys Asn Asn Ser Ala Gly Ala Leu
305 310 315 320

Leu Asp Tyr Val His Thr Ile Arg Leu Gly Gln Asp Leu Trp Glu
325 330 335

<210> SEQ ID NO 11
<211> LENGTH: 335
<212> TYPE: PRT
<213> ORGANISM: Artificial sequence
<220> FEATURE:
<223> OTHER INFORMATION: amino acids 91 to 425 of WP_002935529

<400> SEQUENCE: 11

Met Lys Val Asp Arg Gly Thr Glu Asn Val Val Ser Arg Asn Asp Thr
1 5 10 15

Glu Val Thr Thr Ser Glu Gln Asn Gln Ile Glu Val Thr Glu Thr Lys
20 25 30

Glu Ile Leu Asn Gln Thr Ser Tyr Gln Thr Glu Ser Gly Glu Gln Arg
35 40 45

Gln Ile Ile Trp Ala His Gly Ile Thr Pro Pro Ala Met Glu Gln Ser
50 55 60

Gly Gly Phe Val Lys Glu Lys Tyr Gly Asp Tyr Leu Asn Tyr Thr Ala
65 70 75 80

Pro Phe Lys Ala Gly Lys Gly Tyr Tyr Asp Thr Asn Lys Ser Leu Asn
85 90 95

Ala Ser Phe Ile Asp Leu Asn Leu Cys Phe Ala Ala Val Ser Ser Asn
100 105 110

Met Val His Trp Trp Leu Glu Gln Asn Ser Ser Tyr Val Glu Arg Tyr
115 120 125

Leu Lys Glu Lys Lys Gly Thr Val Asn Val Gly Glu Asn Tyr Ala Ile
130 135 140

Thr Asp Leu Arg Arg Tyr Ile Asp Ser Phe Gln Asp Gln Gln Asn Ser
145 150 155 160

Arg Val Phe Asp Met Phe Lys Thr Tyr Tyr Gly Tyr Arg Thr Asn Gly
165 170 175

Phe Val Ser Asp Ala Leu Val Asp Leu Phe Ile Asn Gly Tyr Lys Pro
180 185 190

Lys Val Gln Gly Gly Val Asn Leu Glu Asp Ser Gln Leu Val Pro Asp
195 200 205

Ser Arg Gly Gly Phe Phe Tyr Asp Val Phe Lys Glu Lys Lys Leu Thr
210 215 220

Asn Arg Ile Phe Ser Gly Ser Tyr Glu Arg Phe Gly Glu Asp Val Arg
225 230 235 240

Thr Val Leu Glu Ser Lys Gly Leu Leu Gly Leu Thr Tyr Arg Thr Leu
245 250 255

Gly Tyr Ala Thr His Ile Val Thr Val Trp Gly Ala Glu Tyr Asp Asn
260 265 270

Gln Gly Lys Ile Arg Ala Val Tyr Ile Thr Asp Ser Asp Asp Gln Gln
275 280 285

```
Glu Gln Ile Gly Leu Lys Arg Met Gly Ile Thr Arg Asp Ala Ser Gly
    290                 295                 300

Asn Pro Arg Leu Asn Asn His Val Lys Asn Asn Ser Ala Gly Ala Leu
305                 310                 315                 320

Leu Asp Tyr Val His Thr Ile Arg Leu Gly Gln Asp Leu Trp Glu
                325                 330                 335


<210> SEQ ID NO 12
<211> LENGTH: 335
<212> TYPE: PRT
<213> ORGANISM: Artificial sequence
<220> FEATURE:
<223> OTHER INFORMATION: amino acids 92 to 426 of WP_015647040

<400> SEQUENCE: 12

Met Lys Val Asp Arg Gly Thr Glu Asn Val Val Ser Arg Asn Asp Lys
1               5                   10                  15

Glu Val Thr Thr Ser Glu Lys Asn Gln Ile Glu Val Thr Glu Thr Lys
            20                  25                  30

Glu Ile Leu Asn Gln Thr Ser Tyr Gln Thr Glu Ser Gly Glu Gln Arg
        35                  40                  45

Gln Ile Ile Trp Ala His Gly Ile Thr Pro Pro Ala Met Glu Gln Ser
    50                  55                  60

Gly Gly Phe Val Lys Glu Lys Tyr Gly Asp Tyr Leu Asn Tyr Thr Ala
65                  70                  75                  80

Pro Phe Glu Ala Gly Lys Gly Tyr Tyr Asp Thr Asn Lys Ser Leu Asn
                85                  90                  95

Ala Ser Phe Ile Asp Leu Asn Leu Cys Phe Ala Ala Val Ser Ser Asn
            100                 105                 110

Met Val His Trp Trp Leu Glu Gln Asn Ser Ser Tyr Val Glu Arg Tyr
        115                 120                 125

Leu Lys Glu Lys Asn Ser Thr Val Asn Val Gly Glu Asn Tyr Ala Ile
    130                 135                 140

Thr Asp Leu Arg Arg Tyr Ile Asn Ser Phe Gln Asn Gln Gln Asn Ser
145                 150                 155                 160

Arg Val Phe Asp Met Phe Lys Thr Tyr Tyr Gly Tyr Arg Thr Asn Gly
                165                 170                 175

Phe Val Ser Asp Ala Leu Val Asp Leu Phe Ile Asn Gly Tyr Lys Pro
            180                 185                 190

Lys Ala Gln Gly Gly Val Asn Leu Glu Asp Ser Gln Leu Val Pro Asp
        195                 200                 205

Ser Arg Gly Gly Phe Phe Tyr Asp Val Phe Lys Glu Lys Lys Leu Thr
    210                 215                 220

Asn Arg Ile Phe Ser Gly Ser Tyr Glu Arg Phe Gly Glu Asp Val Arg
225                 230                 235                 240

Thr Val Leu Glu Ser Lys Gly Leu Leu Gly Leu Thr Tyr Arg Thr Leu
                245                 250                 255

Gly Tyr Ala Thr His Ile Val Thr Val Trp Gly Ala Glu Tyr Asp Asn
            260                 265                 270

Gln Gly Lys Ile Lys Ala Val Tyr Ile Thr Asp Ser Asp Asp Gln Gln
        275                 280                 285

Glu Gln Ile Gly Leu Lys Arg Met Gly Ile Thr Arg Asp Ala Ser Gly
    290                 295                 300

Asn Pro Arg Leu Asn Asn His Val Lys Asn Asn Ser Ala Gly Ala Leu
305                 310                 315                 320
```

```
Leu Asp Tyr Val His Thr Ile Arg Leu Gly Gln Asp Leu Trp Glu
                325                 330                 335


<210> SEQ ID NO 13
<211> LENGTH: 335
<212> TYPE: PRT
<213> ORGANISM: Artificial sequence
<220> FEATURE:
<223> OTHER INFORMATION: amino acids 92 to 426 of WP_023370787

<400> SEQUENCE: 13

Met Lys Ser Asp Asn Gly Asp Glu Asn Ala Val Ser Arg Asp Asp Ser
1               5                   10                  15

Glu Val Thr Thr Asn Glu Gln Asn Gln Ile Glu Val Thr Glu Thr Lys
            20                  25                  30

Glu Ile Leu Asn Gln Thr Ser Tyr Gln Thr Glu Ser Gly Glu Gln Arg
        35                  40                  45

Gln Ile Ile Trp Ala His Gly Ile Thr Pro Pro Ala Met Glu Gln Ser
    50                  55                  60

Gly Gly Phe Val Lys Glu Lys Tyr Gly Asp Tyr Leu Asn Tyr Thr Ala
65                  70                  75                  80

Pro Phe Glu Ala Gly Lys Gly Tyr Tyr Asp Thr Asn Lys Ser Leu Asn
                85                  90                  95

Ala Ser Phe Ile Asp Leu Asn Leu Cys Phe Ala Ala Val Ser Ser Asn
            100                 105                 110

Met Val His Trp Trp Leu Glu Gln Asn Ser Ser Tyr Val Glu Arg Tyr
        115                 120                 125

Leu Lys Glu Lys Lys Gly Thr Val Asn Val Glu Glu Asn Tyr Ala Ile
    130                 135                 140

Thr Asp Ile Arg Arg Tyr Ile Asn Ser Phe Gln Asn Gln Gln Asn Ser
145                 150                 155                 160

Arg Val Phe Asp Met Phe Lys Thr Tyr Tyr Gly Tyr Arg Thr Asn Gly
                165                 170                 175

Phe Val Ser Asp Ala Leu Val Asp Leu Phe Ile Asn Gly Tyr Lys Pro
            180                 185                 190

Lys Ser Gln Gly Gly Val Asn Leu Glu Asp Ser His Leu Val Pro Asp
        195                 200                 205

Ser Arg Gly Gly Phe Phe Tyr Asp Val Phe Lys Glu Lys Lys Leu Thr
    210                 215                 220

Asn Arg Ile Phe Ser Gly Ser Tyr Glu Arg Phe Gly Glu Asp Val Arg
225                 230                 235                 240

Thr Val Leu Glu Ser Lys Gly Leu Leu Gly Leu Thr Tyr Arg Thr Leu
                245                 250                 255

Gly Tyr Ala Thr His Ile Val Thr Val Trp Gly Ala Glu Tyr Asp Asn
            260                 265                 270

Gln Gly Lys Ile Lys Ala Val Tyr Ile Thr Asp Ser Asp Asp Gln Gln
        275                 280                 285

Glu Gln Ile Gly Leu Lys Arg Met Gly Ile Thr Arg Asp Ala Ser Gly
    290                 295                 300

Asn Pro Arg Leu Asn Asn His Met Lys Asn Asn Ser Ala Gly Ala Leu
305                 310                 315                 320

Leu Asp Tyr Val His Thr Ile Arg Leu Gly Gln Asp Leu Trp Glu
                325                 330                 335


<210> SEQ ID NO 14
```

```
<211> LENGTH: 335
<212> TYPE: PRT
<213> ORGANISM: Artificial sequence
<220> FEATURE:
<223> OTHER INFORMATION: amino acids 92 to 426 of WP_044678723

<400> SEQUENCE: 14

Met Asn Ser Asp Asn Gly Asp Glu Asn Val Val Ser Arg Asp Asp Ser
1               5                   10                  15

Glu Val Thr Thr Asn Glu Gln Asn Gln Ile Glu Val Thr Glu Thr Lys
            20                  25                  30

Glu Ile Leu Asn Tyr Thr Ser Tyr Gln Thr Glu Ser Gly Glu Gln Arg
        35                  40                  45

Gln Ile Val Trp Ala Tyr Gly Ile Thr Pro Pro Val Met Glu Gln Lys
    50                  55                  60

Gly Gly Phe Val Lys Glu Lys Tyr Gly Asp Tyr Leu Asn Tyr Thr Ala
65                  70                  75                  80

Pro Phe Glu Ala Gly Lys Gly Tyr Tyr Asp Thr Asn Lys Ser Leu Asn
                85                  90                  95

Ala Ser Phe Ile Asp Leu Asn Leu Cys Phe Ala Ala Val Ser Ser Asn
            100                 105                 110

Met Val His Trp Trp Leu Glu Gln Asn Ser Ser Tyr Val Glu Arg Tyr
        115                 120                 125

Leu Lys Glu Lys Lys Gly Thr Val Asn Val Glu Glu Asn Tyr Ala Ile
    130                 135                 140

Thr Asp Leu Arg Arg Tyr Ile Asn Ser Phe Gln Asn Gln Gln Asn Ser
145                 150                 155                 160

Arg Val Phe Asp Met Phe Lys Thr Tyr Tyr Gly Tyr Arg Thr Asn Gly
                165                 170                 175

Phe Val Ser Asp Ala Leu Val Asp Leu Phe Ile Asn Gly Tyr Lys Pro
            180                 185                 190

Lys Ala Gln Gly Gly Val Asn Leu Glu Asp Ser Gln Leu Val Pro Asp
        195                 200                 205

Ser Arg Gly Gly Phe Phe Tyr Asp Val Phe Lys Glu Lys Lys Leu Thr
    210                 215                 220

Asn Arg Ile Phe Ser Gly Ser Tyr Glu Arg Phe Gly Glu Asp Val Arg
225                 230                 235                 240

Thr Val Leu Glu Ser Lys Gly Leu Leu Gly Leu Thr Tyr Arg Thr Leu
                245                 250                 255

Gly Tyr Ala Thr His Ile Val Thr Val Trp Gly Ala Glu Tyr Asp Asn
            260                 265                 270

Gln Gly Lys Ile Lys Ala Val Tyr Ile Thr Asp Ser Asp Asp Gln Gln
        275                 280                 285

Glu Gln Ile Gly Leu Lys Arg Met Gly Ile Thr Arg Asp Ala Ser Gly
    290                 295                 300

Asn Pro Arg Leu Asn Asn His Met Lys Asn Asn Ser Ala Gly Ala Leu
305                 310                 315                 320

Leu Asp Tyr Val His Thr Ile Arg Leu Gly Gln Asp Leu Trp Glu
                325                 330                 335
```

VACCINE COMPOSITION AGAINST *STREPTOCOCCUS SUIS* INFECTION

CROSS-REFERENCE TO RELATED APPLICATIONS

This application is a continuation of U.S. patent application Ser. No. 15/314,597, filed Nov. 29, 2016, which is a U.S. National Stage application of PCT International Patent Application Serial No. PCT/EP2015/061961, filed May 29, 2015, which itself claims benefit of European Patent Application Serial No. 14170637.4, filed May 30, 2014, each of which is incorporated herein by reference in its entirety.

FIELD OF THE INVENTION

The present invention relates to a vaccine composition and the use thereof for immunization and protection of mammals, in particular pigs and humans, against *Streptococcus suis*.

BACKGROUND OF THE INVENTION

*Streptococcus suis* (*S. suis*) colonizes the respiratory, alimentary and genital tract of pigs. *S. suis* is also one of the most important porcine pathogens, causing different pathologies such as meningitis, septicaemia, arthritis and endocarditis.

*S. suis* infections account for high production losses in the swine industry worldwide. Antibiotics are commonly used to treat *S. suis* infections. But recurrent infections frequently occur as well as the ongoing discussions concerning the reduction of antibiotic usage underline the need for alternative control measures. In Europe, no licensed vaccine is available but autologous bacterins are commonly used. A major drawback is the fact that these vaccines protect only against the homologous serotype. But *S. suis* is a very diverse organism and different serotypes are responsible for morbidity in piglets. Especially serotype 2 strains play an important role for diseases in piglets worldwide.

*S. suis* serotype 2 has been identified to cause meningitis in adults in Asia, but to date no transmission of *S. suis* between humans has been detected.

In general infections elicit an early antigen-specific Immunoglobulin M (IgM) response leading to affinity maturation and isotope switching. Further, IgM antibodies present prior to infection, which are naturally occurring, are important in linking innate to adaptive immunity.

In pigs, IgM is especially important as monomeric membrane IgM (mlgM) as it is the only B-cell receptor occurring since IgD is missing in pigs. Further, IgM synthesis in newborn piglets starts much earlier than IgG and IgA synthesis. IgM in colostrum is crucial for the protection against pathogens which is carried out by complement-mediated killing. Therefore IgM antibodies are important in the protection against different pathogens.

Various virulence or virulence-associated factors of *S. suis* serotype 2 have been identified, among the capsule which is so far the only known essential virulence factor protecting the pathogen against phagocytosis. A number of surface-associated and secreted proteins of *S. suis* serotype 2 exhibit the same or very similar functions as homologous factors of other pathogenic streptococci. A variety of human or animal pathogens such as *Streptococcus pyogenes, Streptococcus equi* subspecies *equi* and *Streptococcus equi* subspecies *zooepidemicus* express specific IgG endopeptidases which are homologue to each other.

A surface-associated or secreted factor with a function unique for *S. suis* has been firstly described by Seele et al. ("Identification of a Novel Host-specific IgM Protease in *Streptococcus suis.*" 2013; Journal of Bacteriology, 195: 930-940). Seele et al. showed that this IgM protease, designated IdeSsuis, does not function as an IgG endopeptidase. The IgM protease degrades opsonising IgM on the bacterial surface and therefore promotes the survival of *S. suis* in blood of bacterin-primed piglets. IdeSsuis is highly specific for IgM and does not cleave IgG or IgA. Seele et al., however, are silent on the function of IdeSsuis, rIdeSsuis and analogues and fragments thereof as effective vaccine against *S. suis* infections. It is merely hypothesized that neutralization of the IdeSsuis IgM protease activity might substantially improve the protective efficacy of bacterins or other future vaccines inducing opsonizing antibodies. However, it is not disclosed that IdeSsuis and related proteins may be used as the exclusive immunizing agent in a vaccine against *S. suis* infections.

Baums et al. disclose in *Surface-associated and secreted factors of Streptococcus suis in epidemiology, pathogenesis and vaccine development, Animal Health Research Reviews*, Volume 10, Issue 01, June 2009, pp 65-83 bacterial factors, both surface-associated and secreted ones, which are considered to contribute to *S. suis* interaction(s) with host factors and cells. Factors are presented with respect to (i) their identification and features, (ii) their distribution among *S. suis* and (iii) their significance for virulence, immune response and vaccination. This review emphasizes the numerous challenging questions remaining to be answered in the future.

The problem to be solved according to the invention is to overcome the problems described in the art and to provide a new vaccine composition to immunize and protect mammals, in particular pigs and humans, against *S. suis* infections.

SUMMARY OF THE INVENTION

This problem is solved, according to the present invention, by providing a vaccine composition which comprises an effective amount of at least one polypeptide or at least one vector selected from the group of (a) a protein designated IdeSsuis, an analogue or a fragment thereof, (b) a protein designated rIdeSsuis, an analogue or a fragment thereof, (c) a vector with a polynucleotide inserted therein encoding the protein IdeSsuis, an analogue or a fragment thereof, (d) a vector with a polynucleotide inserted therein encoding the protein rIdeSsuis, an analogue or a fragment thereof and at least a pharmaceutical carrier, a diluent or an adjuvant.

DETAILED DESCRIPTION OF THE INVENTION

The vaccine composition used in the present invention contains at least one sole polypeptide defined by (a) or (b) together with a pharmaceutical carrier or a diluent or an adjuvant or a mixture thereof. Further the vaccine may also comprise at least one sole vector defined by (c) or (d) with a pharmaceutical carrier, a diluent or an adjuvant or a mixture thereof.

Preferred is a vaccine composition, according to the present invention, wherein IdeSsuis of (a) comprises (a.a) the amino acid sequence of SEQ ID NO: 1;
(a.b) a fragment or an analogue of the amino acid sequence of SEQ ID NO: 1; or
(a.c) a fragment of either (a.a) or (a.b) having an IgM protease activity.

Further preferred is a vaccine composition, according to the present invention, wherein rIdeSsuis of
(b) comprises or consists of
(b.a) the amino acid sequence of SEQ ID NO: 2, 6 or 7;
(b.b) a fragment or an analogue of the amino acid sequence SEQ ID NO: 2, 6 or 7;
(b.c) an amino acid sequence lacking the amino acids from position 1 to 34 of the amino acid sequence SEQ ID NO: 1;
(b.d) an amino acid sequence which is at least 60% homologue, preferably 70% homologue and most preferably 85% homologue to the amino acid sequence of the protein IdeSsuis of SEQ ID NO: 1;
(b.e) a fragment of either (b.a) or (b.b) or (b.c) or (b.d) having an IgM protease activity; or
(b.f) a fragment of either (b.a) or (b.b) or (b.c) or (b.d) comprising or consisting of the amino acid sequence of SEQ ID NO: 5 or an amino acid sequence which is at least 95% homologous thereto.

The amino acid sequence of SEQ ID NO: 2 represents the sequence of SEQ ID NO: 1, however lacking amino acids 1-34 (signal peptide) but adding a HIS tag. It is noted that SEQ ID NO: 1 was derived from the serotype 2 strain of *S. suis*.

The amino acid sequence of SEQ ID NO: 6 represents the N terminal sequence of SEQ ID NO: 2.

SEQ ID NO: 7 (also called antigen rIdeSsuisB2) contains the complete amino acid sequence of the mature IdeSsuis protein of a *S. suis* serotype7 strain but adding a N terminal HIS tag. IdeSsuis protein of a *S. suis* serotype7 strain differs in the C terminal half of the protein since it lacks a sequence of 114 amino acids compared to SEQ ID NO: 1. Amino acids 80 to 414 of SEQ ID NO: 7 (highly conserved part of the so-called Mac-1 domain) correspond in 97.9% to the sequence of SEQ ID NO: 5. The overall identity between SEQ ID NO: 7 and 1 is 96.4% (not considering the N terminal HIS tag and the gap of 114 amino acids).

The term "fragment or analogue" as used herein is defined as follows:

An "analogue" can be regarded as an amino acid sequence similar to the ones disclosed above and showing a level of homology of at least 60%, preferably 70% and most preferably 85% to the original amino acid sequence (e.g. SEQ ID NO: 1, 2, 6 or 7). Also higher degrees of homology, such as 95%, are contemplated herein. Homology, as used herein, means identity. As such, the sequences might differ from each other based on substitution, deletion or insertion.

The degree of identity can be determined with the protein blast program using the blastp algorithm with default parameters which are, for example, Expect threshold: 10, Word size: 3, Matrix: BLOMSUM62, Gap Costs: Existence: 11 Extension: 1 and Compositional adjustments: Conditional compositional score matrix adjustment (BLAST is a registered trademark of the National Library of Medicine). The program can be used to search a protein database using a protein query. Identity reports the exact matches between aligned query and database sequences.

Preferably, amino acid "substitutions" are the result of replacing one amino acid with another amino acid having similar structural and/or chemical properties, i.e., conservative amino acid replacements.

Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, praline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Insertions" or "deletions" are typically in the range of about 1, 2 or 3 amino acids. The variation allowed may be experimentally determined by systematically making insertions or deletions of amino acids in a protein using recombinant DNA techniques and assaying the resulting recombinant variants for activity. This does not require more than routine experiments for a skilled person.

An "analogue" may alternatively or in addition be defined as an amino acid sequence similar to the ones disclosed above and comprising the highly conserved part of the Mac-1 domain (SEQ ID NO: 5) or an amino acid sequence which is at least 95% homologous thereto. The inventors surprisingly found that this domain is mainly responsible for the unexpected immunogenic activity of IdeSsuis proteins and, for itself, is sufficient to provide immune protection to the vaccinated animal. Different serotypes of *S. suis* are existing which partially show large variations in their amino acid sequence thus leading to a level of homology down to about 60%. However, the highly conserved Mac-1 domain shows only small variations between the different serotypes, for example 97.9% between serotype strains 2 and 7.

Therefore, it is acceptable that the amino acids of the present invention (and the nucleic acids encoding the same) show a higher level of variation outside the Mac-1 domain than inside.

The term "fragment" can be defined in a similar way (see above). It describes a shorter amino acid sequence than an analogue (less than about 400 amino acids). It contains or consists of the highly conserved part of the Mac-1 domain (SEQ ID NO: 5) or an amino acid sequence which is at least 95% homologous thereto. Optionally, a fragment can be defined as having an IgM protease activity, although this is not an essential requirement. These fragments may be used as the exclusive active ingredient in a vaccine according to the present invention.

Thus, the vaccine composition of the present invention in a preferred embodiment comprises, essentially consists of or consists of a protein comprising or consisting of the amino acid sequence of SEQ ID NO: 5 or an amino acid sequence which is at least 95% homologous thereto. In an even more preferred embodiment, the protein (or vector encoding the same) is the only active or immunogenic ingredient.

The term "comprising" as used herein in the context of the vaccine composition means that further active or immunogenic components can be present. "Consisting of" means that no further components are present and "essentially consisting of" means that specific further components can be present, namely those not materially affecting the essential characteristics of the vaccine (i.e. inactive or not immunogenic ingredients).

In a preferred embodiment, the present invention provides a vaccine composition essentially consisting of an rIdeSsuis protein which is at least 60%, 70%, 85% or 95% homologous to the amino acid sequence of the protein IdeSsuis of SEQ ID NO: 1 and/or comprises or consists of the amino acid sequence of SEQ ID NO: 5 or an amino acid sequence which is at least 95% homologous thereto.

The above definitions are mutatis mutandis also applicable to the nucleic acid sequences of the present invention encoding these proteins. The homology definitions are the same, the fragment length would be less than about 1,200 nucleic acids.

Further preferred is a vaccine composition, according to the present invention wherein a fragment of the effective amount of said polypeptide of (a) or (b) is part of a fusion protein with at least one other protein.

Preferred is a vaccine composition, according to the present invention, wherein the polynucleotide of (c) comprises a sequence encoding a protein defined as IdeSsuis, namely (a.a) the amino acid sequence of SEQ ID NO: 1;

(a.b) a fragment or an analogue of the amino acid sequence of SEQ ID NO: 1; or (a.c) a fragment of either (a.a) or (a.b) having an IgM protease activity.

Especially preferred is a vaccine composition, according to the present invention, which is characterized in that the polynucleotide comprises (c.a) a sequence of SEQ ID NO: 3 or a complementary sequence thereto; (c.b) a fragment of the sequence of (c.a) or (c.c) a fragment of the sequence of (c.a) which encodes a protein having IgM protease activity.

Further preferred is a vaccine composition, according to the present invention, wherein the polynucleotide of (d) comprises a sequence encoding a protein defined as rIdeSsuis, namely (b.a) the amino acid sequence of SEQ ID NO: 2;

(b.b) a fragment or an analogue of the amino acid sequence SEQ ID NO: 2;

(b.c) an amino acid sequence lacking the amino acids from position 1 to 34 of the amino acid sequence SEQ ID NO: 1;

(b.d) an amino acid sequence which is at least 60% homologue, preferably 70% homologue and most preferably 85% homologue to the amino acid sequence of the protein IdeSsuis of SEQ ID NO: 1; or (b.e) a fragment of either (b.a) or (b.b) or (b.c) or (b.d) having a IgM protease activity, and/or (b.f) a fragment of either (b.a) or (b.b) or (b.c) or (b.d) comprising or consisting of the amino acid sequence of SEQ ID NO: 5 or an amino acid sequence which is at least 95% homologous thereto.

Especially preferred is a vaccine composition, according to the present invention, which is characterized in that the polynucleotide comprises (d.a) a sequence of SEQ ID NO: 4, 8 or 9 or a complementary sequence thereto;

(d.b) a fragment of the sequence of (d.a) or (d.c) a fragment of the sequence of (d.a) which encodes a protein having IgM protease activity Preferred is a vaccine composition, according to the present invention, wherein the polynucleotide is cDNA, DNA or cRNA, RNA. The term "nucleic acid sequence" refers to a heteropolymer of nucleotides or the sequence of these nucleotides. The terms "nucleic acid" and "polynucleotide" are used interchangeably herein to refer to a heteropolymer of nucleotides.

Further it is preferred that a vaccine composition, according to the present invention, is further characterized by the polynucleotide integrated into a vector, wherein the polynucleotide is operably linked to an expression control region of the vector.

This expression vector preferably comprises one or more regulatory sequences. The term "expression vector" generally refers to a plasmid or phage or virus or vector, for expressing a polypeptide from a DNA (RNA) sequence. An expression vector can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

It is also preferred that a vaccine composition, according to the present invention, is provided in a physiologically administrable form and is suitable for intramuscular, intravenous, subcutaneous or dermal injection or mucosal application. It is noted that an intravenous administration is less preferred.

In a further aspect, the present invention is directed to a fragment of IdeSsuis having the amino acid sequence of SEQ ID NO: 5, or an amino acid sequence which is at least 95% homologous thereto. SEQ ID NO: 5 corresponds to the highly conserved part of the Mac-1 domain. Although this domain shows an IgM protease activity, the immunogenic effect is not necessarily linked to this activity. For example, within the scope of the present invention are analogues of SEQ ID NO: 5 where the active center of the protease has been inactivated by mutagenesis of the Cys-residue. Also in this case, the analogue will be effective as a vaccine for eliciting an immune response.

Furthermore, it turned out that amino acid sequences may be effective as a vaccine against *S. suis* infections if they maintain a homology of at least 95% to SEQ ID NO: 5. This includes substitution, insertion or deletion of single amino acids. It turned out that natural occurring Mac-1 domains, although showing some variations, do not differ by more than 5%, or in other words, share an identity of 95% or more in this domain. Exemplary *Streptococcus suis* sequences were obtained from strains isolated in different geographic regions (America, Asia, Europe) and were derived from different host organisms (humans, pigs). These strains belong to different serotypes (1 to 4, 7 to 9, 14 and 16 or which were non-typeable). This is summarized in the enclosed table 1:

| Protein ID | Identity SEQ ID NO: 5 | Strain(s) | Isolated from species | Geographic origin | Serotype |
|---|---|---|---|---|---|
| WP_011922092 | 100% | 05ZYH33 | Human | China | 2 |
| | | P1/7 | Pig | Europe | 2 |
| | | S15W | Pig | United Kingdom | 9 |
| | | S12W | Pig | United Kingdom | 14 |
| WP_044670034 | 100% | E10N | Pig | Vietnam | 2 |
| | | E30Y | Human | Vietnam | 2 |
| WP_012775646 | 100% | JS14 | Pig | China | 14 |

-continued

| Protein ID | Identity SEQ ID NO: 5 | Strain(s) | Isolated from species | Geographic origin | Serotype |
|---|---|---|---|---|---|
| WP_044671938 | 99% | LSOC | Pig | United Kingdom | 1 |
| WP_002935529 | 98% | 89-1591 | Pig | Canada | 2 |
| | | D9 | Pig | China | 7 |
| | | LL-S | Pig | United Kingdom | 3 |
| WP_015647040 | 98% | TL13 | Pig | China | 16 |
| WP_023370787 | 97% | T15 | Pig | Netherlands | 2 |
| | | S97A | Pig | United Kingdom | 4 |
| | | S16Z | Pig | United Kingdom | 8 |
| WP_044678723 | 96% | LS1B | Pig | United Kingdom | Non-typeable |

The sequence information on the Mac-1 domain of proteins WP_044671938, WP_002935529, WP_015647040, WP_023370787 and WP_044678723 is disclosed in SEQ ID NO: 10 to SEQ ID NO: 14.

Since their homology to SEQ ID NO: 5 is higher than 95% they are falling within the definition of a fragment or homologue of the present invention.

A still further aspect is an rIdeSsuis protein comprising the amino acid sequence of SEQ ID NO: 6 or 7, or an amino acid sequence which is at least 60%, preferably 70%, 85% or 95% homologous to the amino acid sequence of the protein IdeSsuis of SEQ ID NO: 6 or 7.

Another object of the present invention is a host cell which is transfected with the vector.

A further object of the present invention is a method for producing a protein defined as rIdeSsuis as a guest antigen in a vector or a different organism, respectively a host cell transfected under condition suitable for expression of said recombinant protein.

A further aspect of the present invention is an antibody which recognizes an IdeSsuis or rIdeSsuis protein, analogue or fragment has defined above.

The antibody is preferably selected from a group, which consists of polyclonal antibodies, monoclonal antibodies, humanized antibodies, chimeric antibodies and synthetic antibodies.

The term “antibody”, is used herein for intact antibodies as well as antibody fragments, which have a certain ability to selectively bind to an epitop. Such fragments include, without limitations, Fab, $F(ab')_2$ and Fv antibody fragments. The term “epitope” means any antigen determinant of an antigen, to which the paratope of an antibody can bind. Epitope determinants usually consist of chemically active surface groups of molecules (e.g. amino acid or sugar residues) and usually display a three-dimensional structure as well as specific physical properties.

The antibodies according to the invention can be produced according to any known procedure. For example the pure complete IdeSsuis or rIdeSsuis protein according to the invention or a fragment/analogue of it can be produced and used as immunogen, to immunize an animal and to produce specific antibodies.

The production of polyclonal antibodies is commonly known. Detailed protocols can be found for example in Green et al, Production of Polyclonal Antisera, in *Immunochemical Protocols* (Manson, editor), pages 1-5 (Humana Press 1992) and Coligan et al, Production of Polyclonal Antisera in Rabbits, Rats, Mice and Hamsters, in *Current Protocols In Immunology*, section 2.4.1 (1992). In addition, the expert is familiar with several techniques regarding the purification and concentration of polyclonal antibodies, as well as of monoclonal antibodies (Coligan et al, Unit 9, *Current Protocols in Immunology*, Wiley Interscience, 1994).

The production of monoclonal antibodies is as well commonly known. Examples include the hybridoma method (Kohler and Milstein, 1975, Nature, 256:495-497, Coligan et al., section 2.5.1-2.6.7; and Harlow et al., *Antibodies: A Laboratory Manual*, page 726 (Cold Spring Harbor Pub. 1988).), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77-96).

In brief, monoclonal antibodies can be attained by injecting a mixture which contains the protein according to the invention into mice. The antibody production in the mice is checked via a serum probe. In the case of a sufficient antibody titer, the mouse is sacrificed and the spleen is removed to isolate B-cells. The B cells are fused with myeloma cells resulting in hybridomas. The hybridomas are cloned and the clones are analyzed. Positive clones which contain a monoclonal antibody against the protein are selected and the antibodies are isolated from the hybridoma cultures. There are many well established techniques to isolate and purify monoclonal antibodies. Such techniques include affinity chromatography with protein A sepharose, size-exclusion chromatography and ion exchange chromatography. Also see for example, Coligan et al., section 2.7.1-2.7.12 and section “Immunglobulin G (IgG)”, in *Methods In Molecular Biology*, volume 10, pages 79-104 (Humana Press 1992).

Preferably, the present invention provides humanized IdeSsuis or rIdeSsuis specific mouse antibodies.

The above antibodies may form part of a parenteral composition for therapeutic treatment of a human or animal (pig) patient suffering from a *S. suis* infection. However, it might be used for prophylactic purposes as well.

In a still further aspect, the present invention is directed to the use of the proteins as disclosed hereinabove for producing the above described antibodies.

Another object of the present invention is the use of the vaccine or parenteral composition, according to the present invention, to perform a prophylactic or metaphylactic or therapeutic treatment of a *Streptococcus suis* infection in pigs. It is further contemplated herein to use the vaccine or the parenteral composition of the present invention for prophylactic or metaphylactic or therapeutic treating an *S. suis* infection in a human patient.

Especially preferred is the use of the vaccine composition, according to the present invention, wherein the treatment causes an immunological response in pigs whereas the immunological response is the activation of a humoral and cellular response against the protein IdeSsuis produced by *Streptococcus suis*.

The treatment (vaccination) involves at least one or two immunizations. The overall dosage administered per pig/human is about 0.05-2.0 mg of protein.

The preparation of the vaccine composition according to the invention is known in the art, and is described in handbooks known to the person skilled in the art. For the production of the vaccine composition according to the present invention pharmaceutically acceptable carriers, diluents or adjuvants which can be used which comprise but are not limited to the following: mineral salt adjuvants (e.g., alum-, calcium-, iron-, zirconium-based), tensoactive adjuvants (e.g., Quil A, QS-21, other saponins), bacteria-derived adjuvants (e.g., N-acetyl muramyl-L-alanyl-D-isoglutamine (MOP), lipopolysaccharides (LPS), monophosphoryl lipid A, trehalose dimycolate (TDM), DNA, CpGs, bacterial toxins), adjuvant emulsions (e.g., FIA, Montanide, Adjuvant 65, Lipovant), liposome adjuvants, polymeric adjuvants and carriers, cytokines (e.g., Granulocyte-macrophage colony stimulating factor), carbohydrate adjuvants, living antigen delivery systems (e.g., bacteria, viruses). Furthermore carriers can also comprise dry formulations such as coated patches made from titan or polymer.

Techniques for formulation and administration of the vaccines of the present application may also be found in "Remington, The Science and Practice of Pharmacy", 22nd edition.

Thus, the present invention is directed to a vaccine composition comprising a protein designated as IdeSsuis or rIdeSsuis or a fragment of either thereof; or a polynucleotide either expressing the protein IdeSsuis or rIdeSsuis or a fragment either thereof which is integrated into an expression vector, whereas the recombinant protein is preferred.

The inventors detected the following:

(a) the induction of opsonising antibodies is crucial for the protective efficacy of a *S. suis* bacterin.

(b) IdeSsuis promotes survival of *S. suis* in blood of vaccinated piglets.

Further the inventors showed, that the vaccination of pigs using the protein rIdeSsuis alone as the sole antigen provides a protection for pigs infected by *S. suis*. According to the invention vaccination with rIdeSsuis prevents the cleavage of IgMs by the IdeSsuis IgM protease of *S. suis* by inducing neutralizing antibodies.

According to the invention, the vaccination of pigs with the recombinant protein rIdeSsuis or a fragment thereof led to high titers of IdeSsuis-specific IgG antibodies with neutralizing activity in contrast to reconvalescent or *S. suis* bacterin immunized piglets. Further, according to Example 1, it has been shown that rIdeSsuis provides a higher immunity against *S. suis* infections than prior art bacterin vaccines.

Further the inventors showed, that the vaccination of pigs with the recombinant protein rIdeSsuis or an analogue or fragment thereof reduces the survival of *S. suis* in the blood.

One important aspect of the present invention—as noted above—resides in the surprising insight that the proteins, nucleic acids and their analogues and fragments as defined hereinabove may be used as the only immunogenic agent for providing protection against *S. suis* infections. No other active ingredients are required, such as bacterins etc. used in the prior art. This is supported by the experimental evidence provided in Example 2. It was shown that the vaccines according to the present invention have a dramatically enhanced efficacy versus placebo/control vaccines, see the Bactericidal Assay data of trials 1 and 2 of Example 2 (FIGS. 3 and 4). The conclusions which can be drawn from the experimental results are as follows:

rIdeSsuis (SEQ ID NO: 2) provides immune protection across different serotyps of *S. suis,*

A protein at least containing the highly conserved Mac-1 domain (SEQ ID NO: 5) is sufficient to provide immune protection, Also IdeSsuis proteins of other serotypes, at least containing the highly conserved Mac-1 domain (SEQ ID NO: 5) induce protection, even if their overall sequence outside this domain differs from that of the serotype 2 strains (even if certain sequence segments are entirely absent).

According to the present invention, the proteins IdeSsuis or rIdeSsuis or analogues/fragments thereof can also be used in fusion proteins. Fusion proteins are created by joining two or more genes which are originally coded for separate proteins. The translation of this fusion gene results in a single or multiple polypeptide with functions derived each from the originally proteins. In the state of the art, fusion proteins are often used to simplify specific applications, such as detection, integration or transport of the protein of interest. A prominent member for detection by fluorescent microscopy is the green fluorescent protein (GFP) fused to the protein of interest.

Other proteins which could be fused to IdeSsuis to improve the delivery and immunogenicity of the antigen are immunoglobulin FC-fragment, non-toxic cholera toxin CTA subunit, mutated heat-labile toxins, *Bacillus subtilis* spore coat protein or bacterial flagellins. Furthermore fusion proteins with proteins of viruses or phages (e.g. modified vaccinia virus Ankara (MVA), Hepatitis B virus, Lambda phage or filamentous bacteriophages like fd, M13 or fl) can be used for the expression of IdeSsuis on the surface of a virus particle or a virus-like particle.

Another possibility to detect fusion proteins is the usage of so called protein tags which are often used during the production of fusion proteins respectively their purification and detection by performing affinity chromatography, western blotting, immunhistochemistry or fluorescent microscopy. Protein tags are commonly short amino acid sequences for example HIS-Tag, myc-Tag, HA-Tag, Step-Tag, GST-Tag, maltose binding protein-Tag or Thioredoxin-Tag.

The method for producing recombinant proteins such as rIdeSsuis, fragments or analogues thereof, according to the present invention is known by the person skilled in the art and also described by handbooks known by the person skilled in the art. In general host cells are used for being transfected with a vector encoding the protein of interest for production of a recombinant protein. In general those host cells may be bacteria (e.g *E. coli, Bacillus* or *Lactococcus* strains), human (e.g. 293-T, HEK-293), mouse cell lines, insect cell lines, yeast cells or plant based systems.

For the transfection of host cells expression vectors such as plasmids (e.g pET, pQE), viruses and phages (e.g. baculovirus, Lambda phage or filamentous bacteriophages) can be used.

Typically vaccine or parenteral compositions are prepared as injectables, either as liquid solutions or suspensions.

The subject of the present invention is also a vaccine or parenteral composition for subcutaneous, intravenous, intramuscular, dermal or mucosal application.

The present vaccines are used to perform a prophylactic or metaphylactic or therapeutic treatment of a *Streptococcus suis* infection in pigs or humans. The treatment involves at least one, preferably two immunizations. Although one single immunization is preferred in practice, a standard immunization usually comprises a prime-boost regimen, i.e. 2 distinct vaccinations. The boost vaccination usually is given in a time frame of 1-3, preferably about 2 weeks after the prime vaccination. The dosage of the individual vaccinations might be the same or different, although it is preferred that the vaccine dosage of both is identical.

The overall dosage which has to be administered to the animal or human patient is about 0.05-2.0 mg of IdeSsuis or rIdeSsuis protein, analogues or fragments as defined hereinabove. Preferred dosages include 0.1-1.0, more preferably about 0.5 mg. This dosage is administered in one dosage should one single vaccination be sufficient. If more than one vaccination is applied, the overall dosage is split in several equal sub-dosages, for example, if two vaccinations are used, the individual dosage of the vaccination is about 0.025-1.0 mg of protein.

The present invention is further described with reference to the following figures, where FIG. 1 shows a time table representing the vaccination challenge experiments with *S. suis* in pigs, FIG. 2 shows a graph representing the results gained with the vaccination challenge experiments of FIG. 1, FIG. 3 shows a diagram of a bactericidal assay involving vaccination with placebo vs. rIdeSsuis, and FIG. 4 depicts a diagram of a bactericidal assay involving vaccination with rIdeSsuis or rIdeSsuis analogues vs. a control group.

Further, a Sequence Listing is attached to this description.

SEQ ID NO: 1 shows the amino acid sequence of the protein IdeSsuis;

SEQ ID NO: 2 shows the amino acid sequence of the recombinant protein rIdeSsuis without the signal peptide;

SEQ ID NO: 3 shows the nucleotide sequence coding for IdeSsuis and SEQ ID NO: 4 shows the nucleotide sequence coding for rIdeSsuis.

SEQ ID NO: 5 shows the amino acid sequence of the highly conserved part of the Mac-1 domain of IdeSsuis.

SEQ ID NO: 6 shows the amino acid sequence of the rIdeSsuis analogue rIdeSsuis_homologue. SEQ ID NO: 7 shows the amino acid sequence of the rIdeSsuis analogue rIdeSsuisB2.

SEQ ID NO: 8 shows the nucleotide sequence coding for rIdeSsuis analogue rIdeSsuis_homologue.

SEQ ID NO: 9 shows the nucleotide sequence coding for rIdeSsuis analogue rIdeSsuisB2.

SEQ ID NO: 10 shows amino acid sequence of amino acids 91 to 425 of WP_044671938.

SEQ ID NO: 11 shows amino acid sequence of amino acids 91 to 425 of WP_002935529.

SEQ ID NO: 12 shows amino acid sequence of amino acids 92 to 426 of WP_015647040.

SEQ ID NO: 13 shows amino acid sequence of amino acids 92 to 426 of WP_023370787.

SEQ ID NO: 14 shows amino acid sequence of amino acids 92 to 426 of WP 044678723.

The following examples shall explain the present invention. The examples shall be understood only as one preferred embodiment of the invention. It is not intended to limit the present invention to the scope of the given examples.

Example 1

The following example provides experimental data after performing vaccination challenge experiments in piglets infected by *S. suis*.

Establishment of vaccination challenge experiments in piglets for different *S. suis* serotypes (serotype 2 and 9) and infection routes (intravenous and intranasal).

Figure 1:
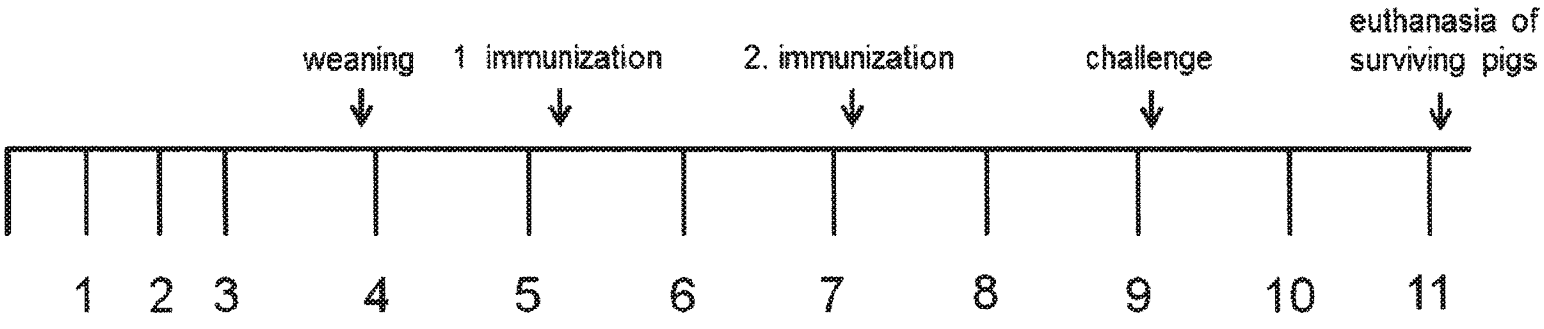

Briefly as shown in FIG. 1, piglets at an age of five weeks were prime vaccinated with a rIdeSsuis vaccine. At an age of 7 weeks these piglets were boostered with rIdeSsuis and in one group also prime vaccinated with a bacterin by intramuscular injection (given in the table in FIG. 1). One group of piglets was only prime vaccinated with a bacterin at an age of 7 weeks and a last group of animals was vaccinated twice with a placebo consisting of buffer and adjuvant. The piglets were challenged two weeks after the second immunizations intranasally. Animals were further monitored every eight hours. For reasons of animal welfare, animals were euthanized in any case in which a piglet exhibits high fever in combination with apathy and anorexia as well as in the case of clinical signs of acute polyarthritis or severe meningitis.

All surviving piglets were sacrificed at 14 days post infection.

Figure 2:
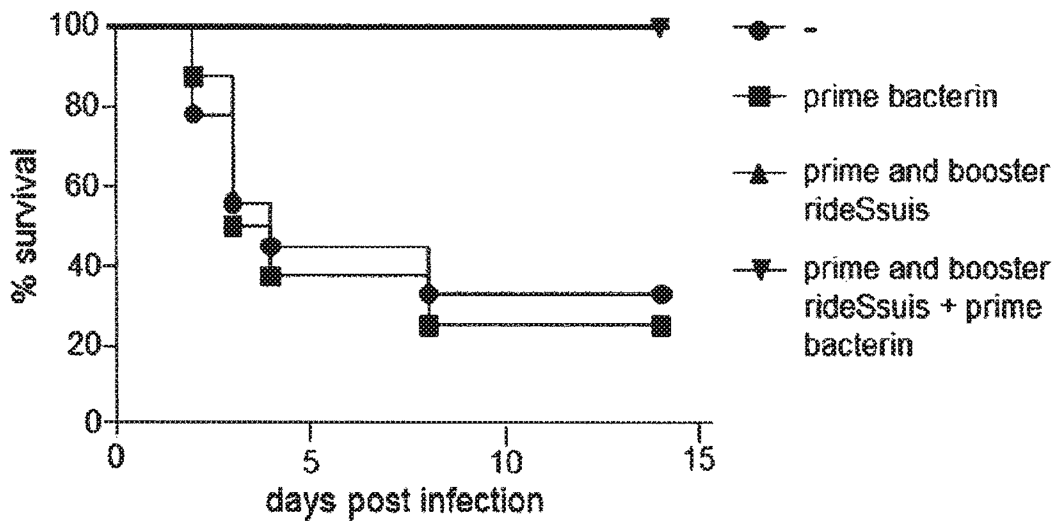

The experiment revealed that the immunization of piglets by using the recombinant protein rIdeSsuis by itself is enough to protect piglets from infections by *S. suis* serotype 2 (FIG. 2).

Example 2

In this example, the bactericidial assay has been used to evaluate the effectiveness of a given vaccine. This test involves the determination of the survival of *S. suis* bacteria of a certain serotype after adding the same to the blood of a test animal. If antibodies protective against a certain serotype are present in the blood of this test animal, the bacteria will be killed during an incubation time of 2 hours efficiently. The extent of protection is designated as "survival factor" (SF) and is the ratio of the colony count after 120 min. and the colony count directly after adding the bacteria to the blood of the test animal. A low survival factor means an efficient killing of the bacteria in the blood and, therefore, an effective protection of the test animal.

The expression and purification of recombinant IdeSsuis (SEQ ID NO: 2), recombinant IdeSsuisB2 (SEQ ID NO: 7) and recombinant IdeSsuis_homologue (SEQ ID NO: 6) was performed by growth of the appropriate strains in LB broth plus ampicillin. Protein expression was induced by adding IPTG. The purification of the recombinant proteins by $Ni^{2+}$-nitrilotriacetic acid affinity chromatography under native conditions was carried out as recommended by the manufacturer (Macherey-Nagel).

Immunization of piglets: Piglets were prime and booster vaccinated with 1.5 ml vaccine containing 0.25 mg rIdeSsuis or 0.25 mg rIdeSsuisB2 or 0.5 mg rIdeSsuis_homologue containing 20% [vol/vol] Emulsigen as an adjuvant.

Trial 1:

Two or four litter mates each are randomly distributed into two trial groups (n=9/group), group 1 control (placebo), group 2 immunized with rIdeSsuis (SEQ ID NO: 2). The animals were immunized and tested according to the following test scheme:

| group | number of pigs | 1. immunization | 2. immunization | bactericidal assay | |
|---|---|---|---|---|---|
| 1 | 9 | Placebo (PBS plus adjuvant) | Placebo (PBS plus adjuvant) | Serotype 2 (St. 10) | Serotype 9 (A3286/94) |
| 2 | 9 | rIdeSsuis (0.25 mg/ piglet) | rIdeSsuis (0.25 mg/ piglet) | Serotype 2 (St. 10) | Serotype 9 (A3286/94) |

Figure 3:
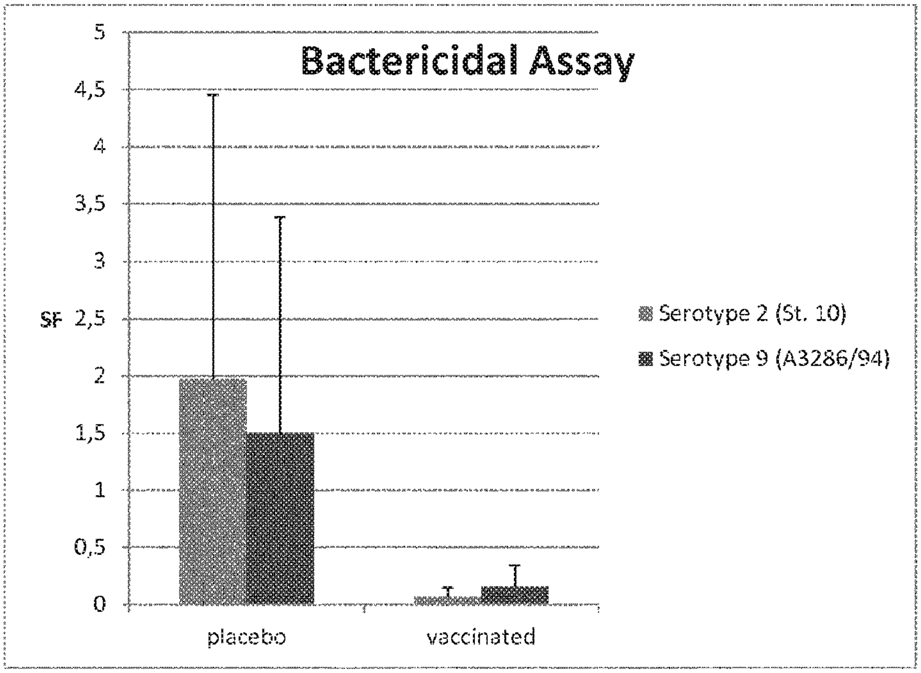
Figure 5:
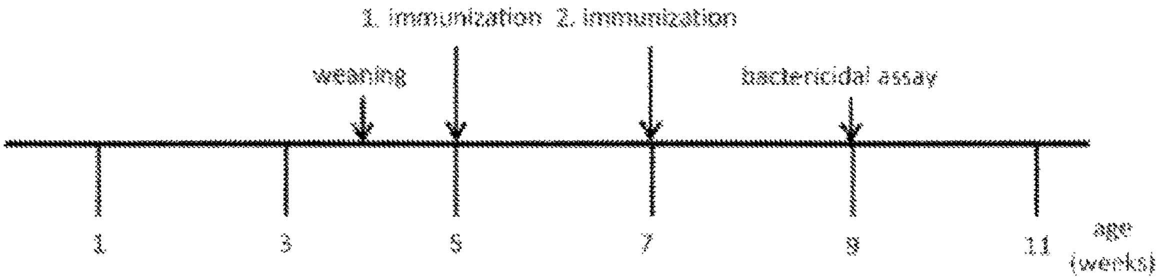
FIG. 5 shows a timetable representing vaccination challenge experiments with *S. suis* in pigs corresponding to the results in FIG. 3.

FIG. 3 shows the results which were achieved according to the test scheme in FIG. 5.

The control group (placebo) showed a much higher survival factor than the vaccinated group. The recombinant antigen rIdeSsuis (group vaccinated), containing the complete sequence of IdeSsuis proteins of serotype 2 strain (SEQ ID NO: 2) induces antibodies effecting an efficient killing of *S. suis* bacteria of strain 2 as well as of strain 9.

Trial 2:

Four litter mates each are randomly distributed into for trial groups (n=6/group with the exception of group 4, where n=S), group 1 control (not immunized), group 2 immunized with rIdeSsuis_homologue (SEQ ID NO: 6), group 3 immunized with IdeSsuis derived from serotype 7 strain (rIdeSsuisB2; SEQ ID NO: 7), group 4 immunized with SEQ ID NO: 2. The animals were immunized and tested according to the following test scheme:

| group | number of pigs | 1. immunization | 2. immunization | bactericidal assay |
|---|---|---|---|---|
| 1 | 6 | no immunization | no immunization | *S. suis* serotype 9 strain A3286/94 |
| 2 | 6 | rIdeSsuis_homologue (0.5 mg/piglet) | rIdeSsuis_homologue (0.5 mg/piglet) | *S. suis* serotype 9 strain A3286/94 |
| 3 | 6 | rIdeSsuisB2 (0.25 mg/piglet) | rIdeSsuisB2 (0.25 mg/piglet) | *S. suis* serotype 9 strain A3286/94 |
| 4 | 5 | rIdeSsuis (0.25 mg/piglet) | rIdeSsuis (0.25 mg/piglet) | *S. suis* serotype 9 strain A3286/94 |

Figure 4:
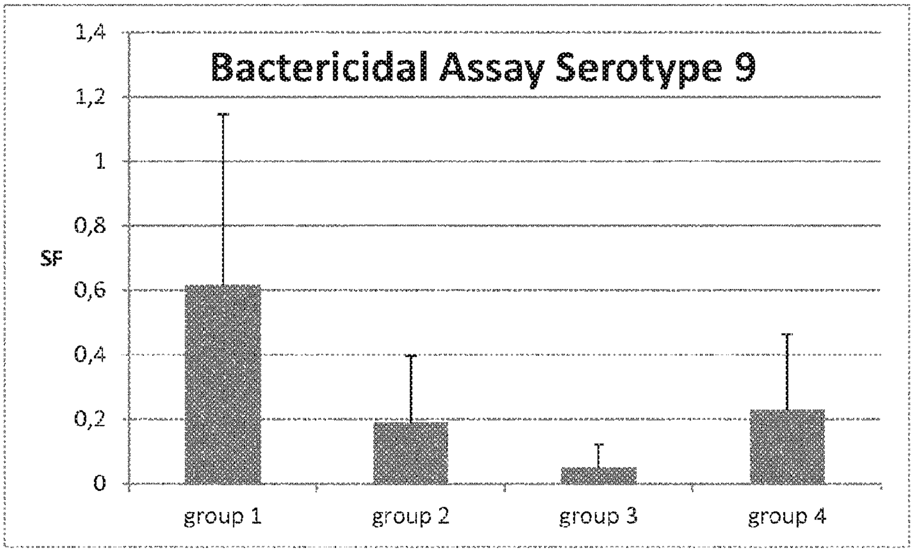
Figure 6:
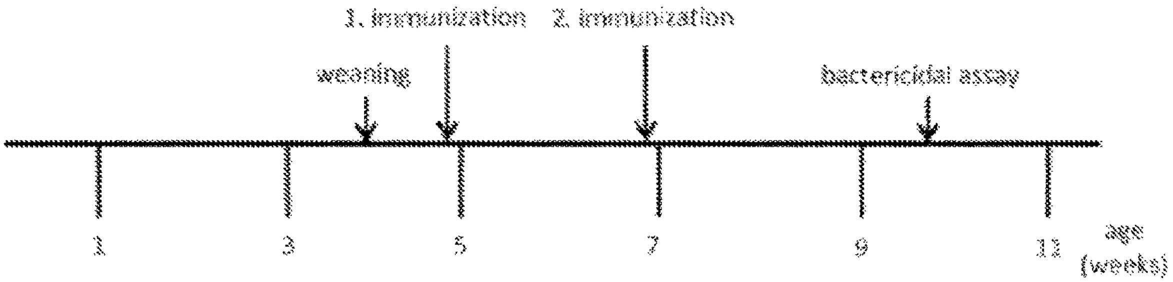
FIG. 6 shows a timetable representing vaccination challenge experiments with *S. suis* in pigs corresponding to the results in FIG. 4.

FIG. 4 shows the results which were achieved following the test scheme in FIG. 6.

The results show a considerably higher survival factor in the control group (group 1) than in the three vaccination groups. The recombinant antigen rIdeSsuis_homologue (group 2), only containing the N-terminal fragment including the highly conserved Mac-1 domain (IgM-Protease-domain), induced antibodies which result in a much better killing of bacteria compared to the control group. The result of group 2 can be compared with those obtained for group 4. Also antigen rIdeSsuis, containing the complete amino acid sequence of mature IdeSsuis protein of a *S. suis* serotype2 strain induces antibodies which reduce the survival of *S. suis* serotype9 strain in the blood considerably. The survival of serotype9 strain is even more compromised by antibodies which have been induced by antigen rIdeSsuisB2 (group 3).

rIdeSsuisB2 (SEQ ID NO: 7) contains the complete amino acid sequence of the mature IdeSsuis protein of a *S. suis* serotype7 strain and differs in the C terminal half of the protein since it lacks a sequence of 114 aa compared to SEQ ID NO: 1. Aa 80 to 414 of SEQ ID NO: 7 (the highly conserved part of the so-called Mac-1 domain) correspond in 97.9% to the sequence of SEQ ID NO: 5. The identity between remaining (-terminal part of SEQ ID NO: 7 and 1 is 96.4%.

The conclusions which can be drawn from the experimental results are as follows:

- rIdeSsuis (SEQ ID NO: 2) provides immune protection across different serotypes of *S. suis,*
- An amino acid at least containing the highly conserved Mac-1 domain is sufficient to provide immune protection,
- Also IdeSsuis proteins of other serotypes, at least containing the highly conserved Mac-1 domain induce protection, even if their overall sequence outside this domain differs from that of the serotype 2 strains (even if certain sequence segments are entirely absent).

What is claimed is:

1. A *Streptococcus suis* vaccine composition comprising an effective amount of at least one polypeptide of SEQ ID NO: 1 comprising the amino acid sequence of SEQ ID NO: 5, wherein an active center of protease consisting of SEQ ID NO: 5 has been inactivated in said polypeptide by mutagenesis of the Cys residue, or one polypeptide of SEQ ID NO: 1 lacking amino acids 1 to 34, and at least a pharmaceutical carrier, a diluent or an adjuvant, wherein said polypeptide induces neutralizing antibodies against *Streptococcus Suis* in pig.

2. The vaccine composition of claim 1, containing an overall amount of about 0.05-2 mg of the polypeptide.

3. The vaccine composition of claim 1, wherein the vaccine composition is provided in a physiologically administrable form and is suitable for intramuscular, intravenous, subcutaneous or dermal injection or mucosal application.

4. A method for prophylactic, metaphylactic or therapeutic treatment of a *Streptococcus suis* infection in a pig or human, the method comprising administering the vaccine composition of claim 1 to the pig or human to elicit an immune response.

5. The method of claim 4, further comprising a second administration of the vaccine composition to the pig or human.

6. The method of claim 5, wherein the overall dosage of the polypeptide is 0.05-2.0 mg.

7. The vaccine composition of claim 1, comprising the polypeptide of SEQ ID NO: 1 and comprising the amino acid sequence of SEQ ID NO: 5, wherein an active center of protease consisting of SEQ ID NO: 5 has been inactivated in said polypeptide by mutagenesis of the Cys residue.

8. The vaccine composition of claim 1, comprising the polypeptide of SEQ ID NO: 1 lacking amino acids 1 to 34.

9. The vaccine composition of claim 1, comprising an adjuvant.

10. A composition comprising at least one polypeptide having an amino acid sequence that is at least 95% homologous to SEQ ID NO:1 and comprising the amino acid sequence of SEQ ID NO:5, wherein an active center of protease consisting of SEQ ID NO: 5 has been inactivated in said polypeptide by mutagenesis of the Cys residue, and at least a pharmaceutical carrier, a diluent or an adjuvant.

* * * * *